US008340759B2

(12) United States Patent
McIntyre et al.

(10) Patent No.: US 8,340,759 B2
(45) Date of Patent: Dec. 25, 2012

(54) LARGE-PITCH COIL CONFIGURATIONS FOR A MEDICAL DEVICE

(75) Inventors: Peter B. McIntyre, Mounds View, MN (US); Bernard Q. Li, Plymouth, MN (US); Ling Wang, Plymouth, MN (US); Shangqian P. Zhang, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 119 days.

(21) Appl. No.: 13/092,367

(22) Filed: Apr. 22, 2011

(65) Prior Publication Data

US 2012/0271381 A1    Oct. 25, 2012

(51) Int. Cl.
*A61N 1/00* (2006.01)
(52) U.S. Cl. .......................................................... 607/2
(58) Field of Classification Search ................ 607/2
See application file for complete search history.

(56) References Cited

U.S. PATENT DOCUMENTS

| | | | |
|---|---|---|---|
| 4,678,868 A | 7/1987 | Kraska et al. | |
| 5,169,597 A | 12/1992 | Davidson et al. | |
| 5,330,521 A | 7/1994 | Cohen | |
| 5,477,864 A | 12/1995 | Davidson | |
| 5,483,022 A | 1/1996 | Mar | |
| 5,522,875 A * | 6/1996 | Gates et al. | 607/127 |
| 5,685,306 A | 11/1997 | Davidson | |
| 5,871,595 A | 2/1999 | Ahmed et al. | |
| 6,238,491 B1 | 5/2001 | Davidson et al. | |
| 6,402,859 B1 | 6/2002 | Ishii et al. | |
| 6,409,852 B1 | 6/2002 | Lin et al. | |
| 6,720,497 B1 | 4/2004 | Barsne | |
| 6,752,882 B2 | 6/2004 | Lin et al. | |
| 6,800,153 B2 | 10/2004 | Ishii et al. | |
| 6,950,709 B2 | 9/2005 | Baudino | |
| 7,015,392 B1 | 3/2006 | Dickenson | |
| 7,130,700 B2 | 10/2006 | Gardeski et al. | |
| 7,174,220 B1 | 2/2007 | Chitre et al. | |
| 7,261,782 B2 | 8/2007 | Hwang et al. | |
| 7,519,432 B2 | 4/2009 | Bolea et al. | |
| 7,571,010 B2 | 8/2009 | Zarembo et al. | |
| 7,612,291 B2 | 11/2009 | Chastain et al. | |
| 7,722,805 B2 | 5/2010 | Hao et al. | |
| 2002/0174922 A1 | 11/2002 | Ishii et al. | |

(Continued)

FOREIGN PATENT DOCUMENTS

EP        1083243 A3    3/2006

(Continued)

OTHER PUBLICATIONS

International Search Report and Written Opinion dated Jul. 4, 2012, from co-related international application, PCT/US2012/030671.

(Continued)

*Primary Examiner* — George Manuel
(74) *Attorney, Agent, or Firm* — Beth L. McMahon

(57) ABSTRACT

Techniques related to coils for medical device are disclosed. One example coil may comprise multiple filars, each being formed of a biocompatible beta titanium alloy having an elastic modulus ranging from 30 GigaPascals (GPa) to 90 GPa and comprising at least two elements from a group consisting of titanium, molybdenum, niobium, tantalum, zirconium, chromium, iron and tin. At least one of the multiple filars may be electrically insulated one from another. A structural body, such as a lead body, may carry the coil. One or more filars may carry a low-resistance core.

40 Claims, 22 Drawing Sheets

U.S. PATENT DOCUMENTS

| | | |
|---|---|---|
| 2003/0009095 A1 | 1/2003 | Skarda |
| 2004/0158309 A1 | 8/2004 | Wachter et al. |
| 2005/0070990 A1 | 3/2005 | Stinson |
| 2005/0072496 A1 | 4/2005 | Hwang et al. |
| 2007/0137742 A1 | 6/2007 | Hao et al. |
| 2008/0195194 A1 | 8/2008 | Pacetti et al. |
| 2008/0294207 A1 | 11/2008 | Kast et al. |
| 2008/0312740 A1 | 12/2008 | Wachter et al. |

FOREIGN PATENT DOCUMENTS

| | | |
|---|---|---|
| WO | WO9945161 A1 | 9/1999 |
| WO | WO2009145406 A1 | 12/2009 |

OTHER PUBLICATIONS

Iman, et al, "Titanium Alloys as Implant Materials", ASTM Special Technical Publication, Philadelphia, PA, US, No. 1272, Nov. 16, 1994, pp. 3-16.

Ribeiro, AL., Mechanical, physical, and chemical characterization of Ti—35Nb—5Zr and Ti—35Nb—10Zr casting alloys, J Mater Sci Mater Med. Aug. 2009;20(8):1629-36. Epub Apr. 1, 2009.

Ti-075 Ti—15Mo.pdf, (Jan. 31, 2011).

http://en.wikipedia.org/wiki/Titanium_alloy, (May 23, 2012).

* cited by examiner

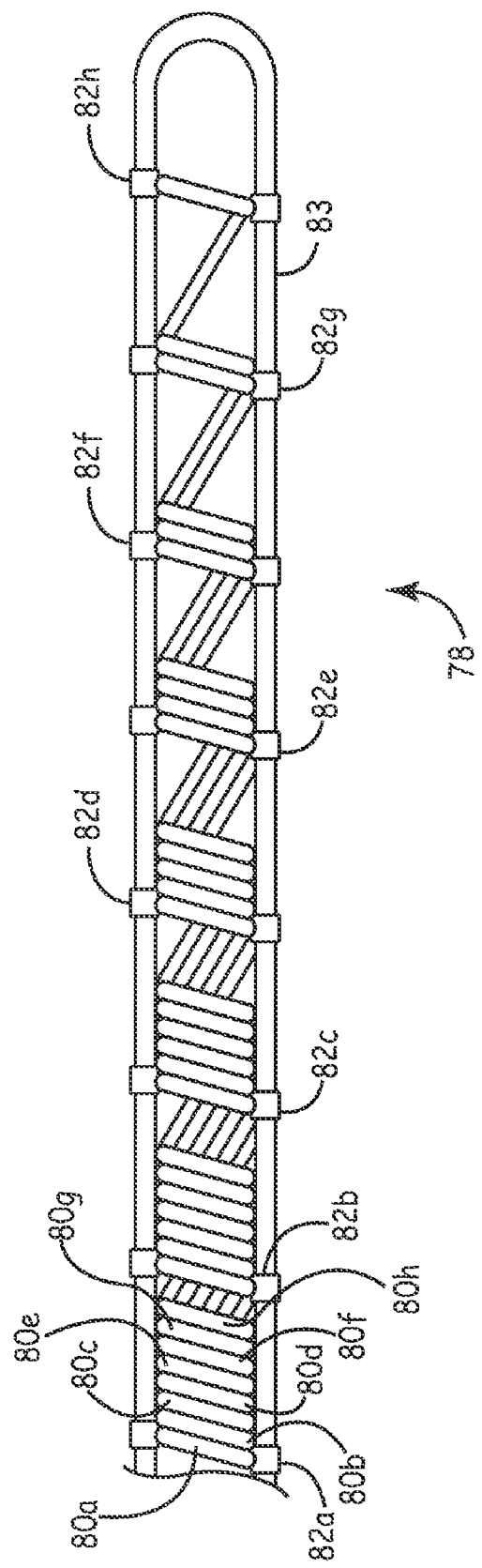

LARGE-PITCH COIL CONFIGURATIONS FOR A MEDICAL DEVICE

FIELD

This disclosure relates to a medical apparatus and more particularly to a coil configurations for a medical apparatus such as a lead or lead extension.

BACKGROUND

The medical device industry produces a wide variety of electronic and mechanical devices for treating patient medical conditions such as pacemakers, defibrillators, neurostimulators and therapeutic substance delivery pumps. Medical devices can be surgically implanted or connected externally to the patient receiving treatment. Clinicians use medical devices alone or in combination with therapeutic substance therapies and surgery to treat patient medical conditions. For some medical conditions, medical devices provide the best and sometimes the only therapy to restore an individual to a more healthful condition. One type of medical device is an implantable stimulation system that can be used to treat conditions including, but not limited to, pain, movement disorders, pelvic floor disorders, gastroparesis, and a wide variety of other medical conditions. Such a system may be connected to a stimulation lead with or without extension. The lead may carry one or more elements such as electrodes and/or other sensors that may be electrically coupled to the system to deliver electrical stimulation and/or to sense signals from the patient's body. These elements may be electrically coupled to the system via one or more wires configured as coils or cables, for instance.

SUMMARY

Techniques related to coils for medical devices, including implantable medical devices, are disclosed. One example coil may comprise multiple filars, each being formed of a biocompatible beta titanium alloy having an elastic modulus ranging from 30 GigaPascals (GPa) to 90 GPa and comprising at least two elements from a group consisting of titanium, molybdenum, niobium, tantalum, zirconium, chromium, iron and tin. At least one of the multiple filars may be electrically insulated one from another. A structural body, such as a lead body, may carry the coil.

In one example, the coil may have a large pitch and large filar count. For instance the coil may have twelve or more filars with a pitch of up to 0.10 inches. In a particular embodiment, a coil having twelve filars with a pitch of 0.08 inches is disclosed. This coil may have an outer diameter of less than 0.03 inches. In such examples, a ratio of pitch of the coil to outer diameter of the coil may be relatively large (e.g., this ratio may be "three" in some embodiments.) Such a coil has a relatively small profile while being capable of transmitting a large number of signals. An example coil with twelve filars may transmit up to twelve signals simultaneously. Moreover, because of the low modulus of the beta titanium alloy, the coil will be flexible and exhibit a relatively small bend radius at yield. This allows the coil to be more easily navigated to a target therapy location within a body of a patient and also enhances patient comfort.

In one embodiment, at least one of the filars of the coil may include a low-resistance core. The core may be formed of a material having a resistivity of less than 25 micro-ohm-cm. The material forming the core may be one of silver, tantalum, a tantalum alloy, niobium, a niobium alloy, platinum, a platinum alloy, palladium, or a palladium alloy. Inclusion of a core within a filar allows the resistance of the filar to be tuned. For instance, tuning may be accomplished by selecting the ratio of a cross-sectional area of the core to a cross-sectional area of the filar. By tuning the resistance of the filar to be the same as, or similar to, a resistance of an element to which the filar is interconnected, a quality of signal transmission can be improved. For instance, there may be fewer reflections.

Another example of the disclosure provides a method comprising winding a coil of multiple filars, each being formed of a biocompatible beta titanium alloy having an elastic modulus ranging from 30 GigaPascals (GPa) to 90 GPa and comprising at least two elements from a group consisting of titanium, molybdenum, niobium, tantalum, zirconium, chromium, iron and tin. At least one of the filars is provided with an insulating layer to electrically insulate the filar from the other filars. Each of the filars may have an insulating layer such that all filars are insulated from all other filars. A ratio of pitch of the coil to outer diameter of the coil may be greater than one.

The foregoing method may further comprise incorporating the coil into a medical device adapted to perform at least one of delivering therapy to a patient or sensing a signal from the patient. The method may also include electrically coupling one or more of the filars each to a different respective one of multiple elements (e.g., such as electrodes) that are carried by the medical device. The method may also involve tuning a resistance of one or more of the coil filars so that each such filar has substantially a same resistance as a resistance of the respective element to which the filar is electrically coupled, as described above.

Another example according to the disclosure includes a medical electrical lead. The lead may include a lead body and a coil comprising multiple filars, each being formed of a biocompatible beta titanium alloy having an elastic modulus ranging from 30 GigaPascals (GPa) to 90 GPa and comprising at least two elements from a group consisting of titanium, molybdenum, niobium, tantalum, zirconium, chromium, iron and tin. At least one of the multiple filars may be electrically insulated from the other filars. The coil may contain at twelve filars and have an outer diameter of less than 0.03 inches. The pitch of the coil may be substantially about 0.08 inches.

Other aspects of the disclosure will become apparent to those skilled in the art from the following description and the accompanying drawings.

BRIEF DESCRIPTION OF THE DRAWINGS

FIG. 10C is a conceptual drawing of a side cut-away view of a coil containing eight filars, each being coupled to a respective one of eight electrodes.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

Figure 1:
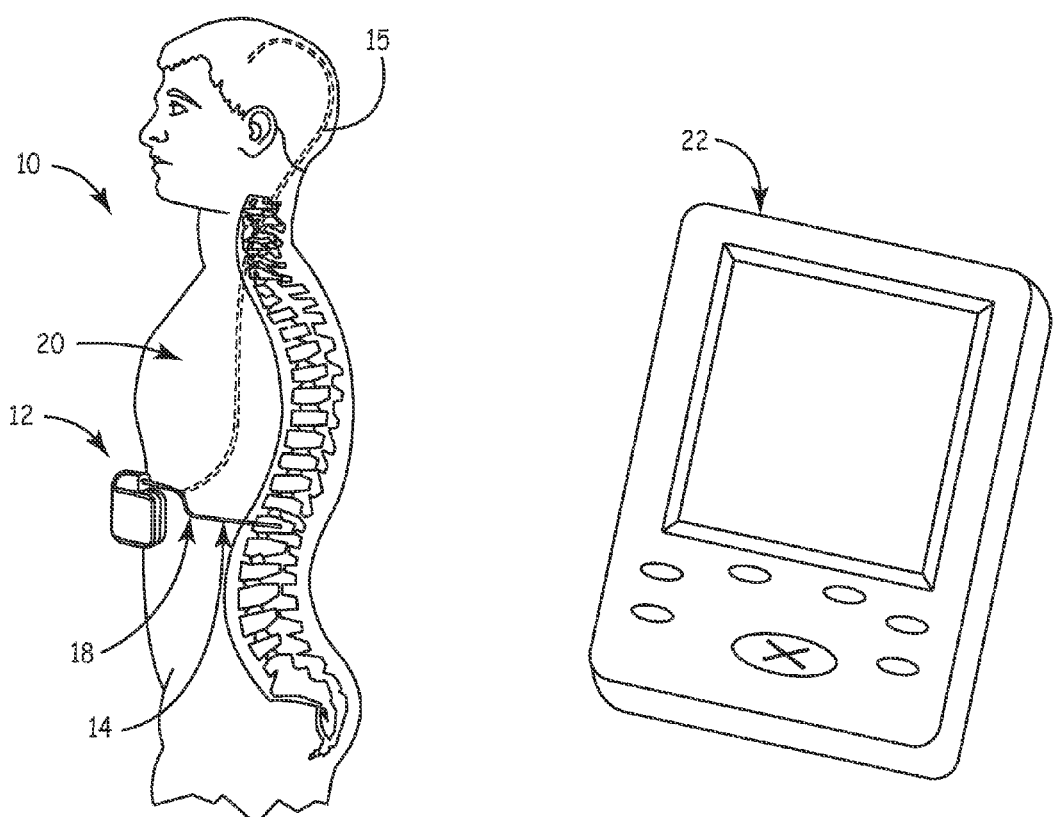
FIG. 1 shows one example system that may usefully employ the techniques and mechanisms of the current disclosure.

FIG. 1 shows one exemplary environmental view 10 of an implantable medical device (IMD 12 that may usefully employ the techniques and mechanisms of the current disclosure. While this example displays an implantable neurostimulation system embodiment, other medical systems, including cardiac systems and other systems used to delivery therapy to, and/or sense signals from, a living body may employ the concepts disclosed herein.

The IMD 12 of the type shown in view 10 may be used to treat conditions such as pain, movement disorders, pelvic floor disorders, gastroparesis, incontinence, sexual disfunction, and a wide variety of other medical conditions. The IMD 12 is typically implanted subcutaneously in the patient's body 20 at a location selected by the clinician. A stimulation lead 14, which may be coupled to IMD 12 via a lead extension 18, may be fixed in place near the location selected by the clinician using a device such as an anchor. A programmer 22, which may be a clinician or patient programmer, may be used to program IMD 12 to deliver electrical stimulation via one or more conducting electrodes located along lead 14.

In FIG. 1, lead 14 is shown specifically providing therapy in the patient's back region. Such therapy may include delivering spinal cord stimulation (SCS), peripheral nerve stimulation (PNS), and peripheral nerve field stimulation (PNFS), for example, as may be used to treat pain.

In other examples, one or more leads 15 (shown dashed) may by coupled to IMD 12 via a lead extension to deliver therapy to a patient's brain. For instance, deep brain stimulation (DBS) or cortical stimulation (CS) may be used to treat a number of neurological conditions, including, e.g., depression, dementia, obsessive-compulsive disorder, migraines, eating disorders, and movement disorders, such as Parkinson's disease, spasticity, epilepsy, and dystonia. One or more leads such as lead 15 may be placed at any location within the brain of the patient, including the pedunculopontine nucleus (PPN), thalamus, basal ganglia structures (e.g., globus pallidus, substantia nigra, subthalmic nucleus), zona inserta, fiber tracts, lenticular fasciculus (and branches thereof), ansa lenticularis, and/or the Field of Forel (thalamic fasciculus). In the case of migraines, leads 15 may be implanted to provide stimulation to the visual cortex of brain in order to reduce or eliminate migraine headaches afflicting the patient. Additionally, leads 15 may be implanted to provide stimulation to the cerebral cortex of brain for the treatment of epilepsy. The target therapy delivery site may depend upon the patient condition or disorder being treated. Of course, as discussed above, leads may extend to other locations in the body beyond what is illustrated in FIG. 1 to treat other medical conditions, and the conditions specifically mentioned above are merely examples.

Figure 2:
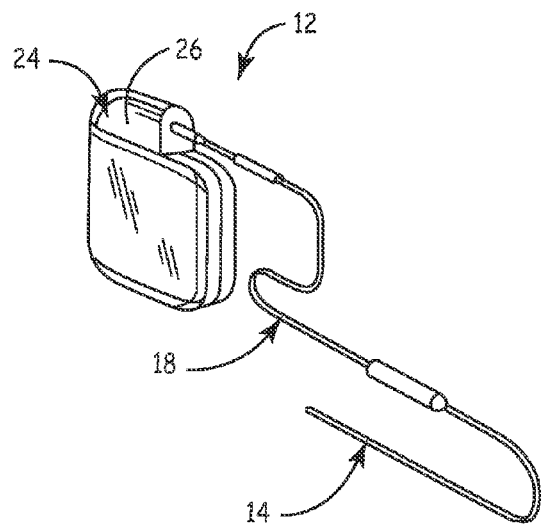
FIG. 2 shows an example implantable neurostimulation system.

FIG. 2 shows IMD 12, a stimulation lead 14, and a lead extension 18. The IMD 12 has a housing 24 (a "can"), a power supply (e.g., a battery or capacitor) carried in the housing 24, and stimulation electronics which may be powered by the power supply. These electronics may be coupled to a connector block 26, which is also known as a terminal block.

Figure 3A:
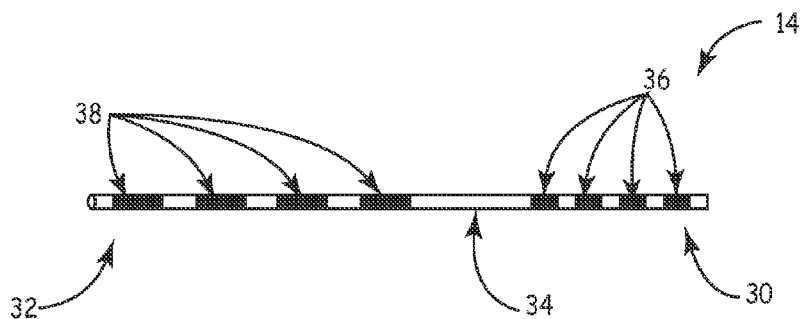
FIG. 3A is a side view of one embodiment of a stimulation lead.

FIG. 3A is a side view of one embodiment of stimulation lead 14. The stimulation lead 14 has a lead proximal end 30, a lead distal end 32 and a structural body 34 which may be formed of a material that is an electrical insulator in one example. The lead distal end 32 has one or more conducting electrodes 38 to deliver electrical stimulation to a living body or to receive an electrical signal from the body. The lead proximal end 30 includes one or more connector electrodes 36 (also known as electrical terminals) to electrically couple the one or more conducting electrodes 38 to stimulation electronics inside IMD 12, optionally through lead extension 18.

Using stimulation electronics within IMD 12, any one or more of the conducting electrodes 38 may be activated as cathodes and one or more others of these electrodes may be activated as anodes to deliver stimulation to the patient. Alternatively or additionally, an electrode on the case of IMD 12 may serve as an anode or cathode. In some instances, some or all of electrodes 38 may be employed to sense signals from a patient's body. In some embodiments, such sensing of signals may be time-multiplexed with delivery of therapy via these electrodes.

In one embodiment, conducting electrodes 38 may be ring electrodes that encircle the circumference of the body of lead 14. Alternatively, electrodes having a different geometry may be carried by the lead. For instance, segmented electrodes may be employed that extend over a portion of the circumference of the lead body.

Figure 3B:
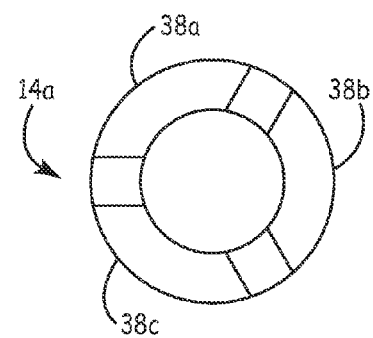
FIG. 3B is a cross-sectional view of an array of segmented electrodes.

FIG. 3B is a cross-sectional view of an example of a stimulation lead 14a carrying at least three segmented electrodes 38a, 38b, and 38c. The segmented electrodes may be used to deliver electrical stimulation to a more localized area of tissue. For instance, by activating electrode 38a, tissue adjacent to this electrode may be stimulated while tissue residing near electrode 38c may not be stimulated.

In one example, the array of electrodes 38a, 38b, and 38c may be substituted in place of a single ring electrode. For instance, in reference to lead 14 of FIG. 3A, an array of electrodes 38a-38c may substituted for each of the four electrodes 38 such that lead 14 carries a complex array of twelve conducting electrodes along its lead body. In such an embodiment, it may be desirable to likewise provide twelve connector electrodes 36, each to couple a respective one of the conducting electrodes to the stimulation electronics of IMD 12. As in the scenario described above with respect to FIG. 3A, any one or more of these twelve segmented conducting electrodes may be activated as cathodes and one or more other electrodes may be activated as anodes. Alternatively or additionally, an electrode on the can of IMD 12 may be activated as an anode or cathode. A complex electrode array of this type will allow for generation of a more complex electrical field and may provide more targeted stimulation. This may be beneficial in the treatment of various conditions, including those associated with pain. As a specific example, this may be beneficial when DBS therapy is being delivered, since such an array may provide stimulation to very localized areas in a patient's brain to optimize treatment and minimize side effects.

Within a body of a lead such as lead 14 or lead 14a, there is at least one wire (not shown) to electrically connect a conducting electrode (e.g., electrodes 38, 38a-38c) to a respective connector electrode (e.g., electrodes 36.) Many factors may be taken into account when determining what type of wire should be used for this purpose. On the one hand, it may be desirable to utilize a material possessing a low resistivity to form the wire. This will result in a minimum voltage drop between the conducting electrode 38 and the connector electrode 36 to which it is coupled as well as minimal power loss within the wire. Silver may be used to form a wire that meets these objectives.

Limitations exist with selecting a low-resistivity material alone to serve as the wire. Materials such as silver do not have tensile strength and easily oxidize. Therefore, bending and twisting a wire made solely of silver may result in weakening of the wire so that a lead containing the wire may require replacement more quickly.

One way to address the foregoing limitations is to surround a low-resistance core (e.g., a silver core) with another material that can provide additional strength. In the past, MP35N (CoNiCrMo) was used for this purpose.

Figure 4A:
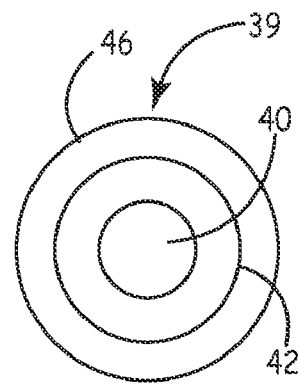
FIG. 4A is a cross-sectional view of one embodiment of a wire that may be used to electrically couple one or more conducting electrodes to one or more connector electrodes.

FIG. 4A is a cross-sectional view of one embodiment of a wire 39 that may be used to electrically couple one or more conducting electrodes 38 to one or more connector electrodes 36. The wire 39 includes a low-resistance core 40 that is capable of providing a low-resistant path between a conducting electrode 38 and a connector electrode 36. The core 40 is directly surrounded in one embodiment by a tube 42 formed of a biocompatible, corrosion-resistant material having a tensile strength that is substantially higher than the core. As discussed above, the biocompatible material used for this purpose has typically been MP35N with core 40 being made of silver.

Wire 39 may be electrically insulated by a insulating layer 46, which may be a polymer. The polymer could be, but is not limited to, ethylene tetrafluoroethylene (ETFE), polytetrafluoroethylene (PTFE), silicone rubber or polyurethane. Other materials that act as electrical insulators may be used in the alternative.

A wire 39 of the type shown in FIG. 4A that is made of MP35N having a silver core is difficult to manufacture. During the manufacturing process, a tube 42 of MP35N is formed that has a diameter of about 0.25 cm-1.00 cm. The low-resistance core 40, which in this example may be silver, is threaded into this tube. The tube 42 and the inner core 40 are drawn to obtain a wire having a smaller diameter. The drawn wire may then be heated and re-drawn to form an even smaller wire. The steps of drawing, and then heating, the tube 42 and the core 40 are repeated multiple times until a wire having a sufficiently small diameter is obtained.

As discussed above, to draw the tube 42 to form a wire having the desired diameter, the tube is heated to a desired annealing temperature at which the material becomes flexible. MP35N must generally be annealed at a relatively high temperature above 1000° C. before it can optimally be drawn. However, the melting point of low-resistivity materials of the type used to form core 40 is generally below such high temperatures. For instance, the melting point of silver is around 960° C.

In view of the foregoing, at the optimal temperature for heating and drawing an MP35N tube 42, the core material will be melted. As a result, some of the molten core material may exit (i.e., "run out of") the ends of the tube 42, making the ends of the resulting wire unusable. Moreover, the liquefied core material that is located within the center away from the ends of the tube 42 will expand and exert pressure on the inside of the tube. This creates bulges in the tube 42 before and during the drawing process. The portions of the wire 39 having such imperfections will be discarded after the drawing process is completed, resulting in manufacturing waste and lower yields.

To prevent the foregoing from occurring, heating may be limited to something much less than what is optimal for MP35N. For instance, heating of a wire containing an MP35N tube 42 surrounding a silver core may be limited to something under 960° C. to prevent melting of the silver core. However, at this temperature, the MP35N is relatively brittle (has a low ductility), making the material difficult to work, and further complicating the manufacturing process. Moreover, the embrittled MP35N wire cannot withstand the repeated stress and strains of the type that is present in typical implant scenarios (e.g., as in repeated flexing of a lead body). Thus, such devices may not have as long of a life, requiring explant or replacement sooner than would otherwise be the case.

Another option for addressing the foregoing challenges may involve threading core 40 into tube 42 after the tube has been drawn to the desired length and diameter. However, after the tube has been drawn, the tube will have a very small diameter and a very long length. This makes the threading process difficult, if not impossible in some cases.

The foregoing challenges are addressed by an improved wire 39 that may use a low-resistance core 40 such as silver or another low-resistivity material that may be directly surrounded by a tube 42 of a biocompatible beta titanium alloy. As known in the art, beta titanium alloys exhibit the body center cubic (BCC) structure of titanium. This is in contrast to alpha titanium alloys which exhibit the hexagonal close pack (HCP) form of the element. Biocompatible beta titanium alloys may include as a major alloy one or more of the elements titanium, molybdenum, niobium, tantalum, zirconium, chromium, iron and tin. Specific examples of biocompatible beta titanium alloys that may be used according to this disclosure include Ti-15Mo, TiOsteum (Ti-35Nb-7Zr-5Ta), TNTZ (Ti-29Nb-12Ta-5Zr), TNCS (Ti-19Nb-5Cr-4Sn), Ti—Nb—Cr—Zr (Ti-20Nb-5Cr-4Zr), TMFZ, TLM (Ti-22Nb-3Zr-3Mo-2Sn) and Ti-30Ta, although these examples are not limiting. Of course, in addition to the major alloys listed above, these alloys may include trace amounts of other elements such as silicon (Si), boron (B), or oxygen (O) which may be added, in one example, to achieve a smaller grain size.

Figure 4B:
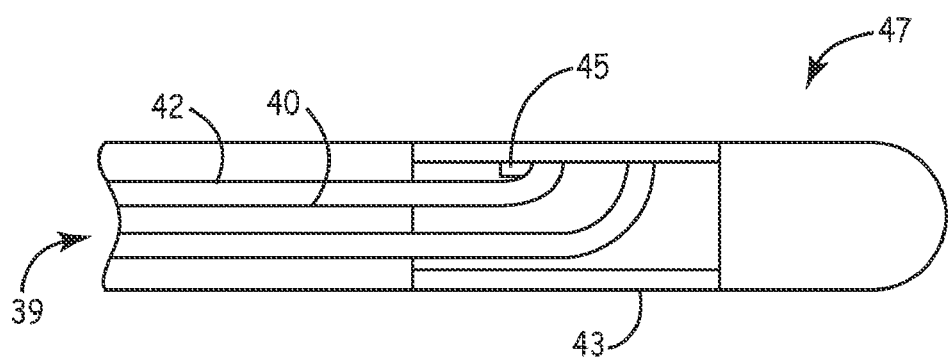
FIG. 4B is a side cutaway view of a distal end of a lead carrying a beta titanium wire having a low-resistance core electrically and mechanically coupled to an electrode.

An insulating layer 46 may be provided surrounding the beta titanium layer. The insulating layer 46 may be any of the polymers set forth above. An example use of such a wire is shown in FIG. 4B and will be discussed further below.

The following Table 1 provides some examples of biocompatible beta titanium alloys, although these examples should not be considered limiting.

TABLE 1

|  | Ti | Nb | Ta | Zr | Cr | Sn | Mo |
|---|---|---|---|---|---|---|---|
| TNTZ | Balance | 29 | 12 | 5 |  |  |  |
| TiOsteum | Balance | 35 | 5 | 7 |  |  |  |
| TNCZ | Balance | 20 |  | 4 | 5 |  |  |
| TNCS | Balance | 18.6 |  |  | 4.5 | 4 |  |
| Ti—45Nb | Balance | 45 |  |  |  |  |  |
| Ti—30Ta | Balance |  | 30 |  |  |  |  |
| Ti—15Mo | Balance |  |  |  |  |  | 15 |
| TLM | Balance | 22.4 |  | 2.8 |  | 1.8 | 2.7 |

A wire formed of a beta titanium alloy may be readily manufactured without the challenges discussed above associated with the need to use a low annealing temperature. For instance, an unbroken tube may be formed of the selected biocompatible beta titanium alloy. In this example, the tube may have an inner diameter of between 0.25 cm-5.0 cm. A low-resistance core may be inserted into the tube, with the core being formed of a material that may have a resistivity of less than 25 micro-ohm-cm ($\mu\Omega$-cm) in one example. In some examples, the resistivity of the core material may be between 10 micro-ohm-cm and 20 micro-ohms-cm. Examples of materials that may be used to form low-resistance cores include silver, tantalum, tantalum alloys (containing Mo, Nb, Zr, W, Pt, and/or Pd), niobium, niobium alloys (containing Ta, Mo, Zr, W, and/or Pt), platinum and platinum alloys, and palladium and palladium alloys (containing Re and Rh). Any biocompatible materials possessing resistivities in these ranges may be used instead.

Next, a cold drawing process may be used wherein the core 40 inserted within tube 42 is drawn through a die structure, resulting in a wire having a reduced diameter. Thereafter, the wire is annealed by heating it to at least the beta transit temperature of the selected titanium alloy. At this temperature, the alloy undergoes a phase transformation from the alpha & beta phase to full beta phase. For beta titanium alloys, the beta transit temperature will be in a range of 600° C.-900° C. For instance, in one embodiment, Ti-15Mo has a beta transit temperature of around 730° C. Thus, annealing may occur at between 730° C.-815° C. in one example. This annealing process of using these temperatures to anneal the alloy changes the physical characteristics of titanium alloy tube 42. That is, it prevents tube 42 from becoming brittle, and will allow an additional cold-drawing step to be performed without the risk of the tube 42 cracking. Since the annealing temperature of the beta titanium alloy is lower than the melting point of the material used to form the low-resistance core (e.g., silver), the core material will not melt when the wire is annealed. Therefore, the challenges discussed above with respect to silver-cored MP35N wires can be avoided.

After annealing the wire, the wire may again be cold-drawn through another die structure having a still-smaller diameter followed by yet another annealing step. Any number of such iterations may be performed to obtain a wire having a desired diameter. In one example, the final wire may have a low-resistance core that is, in one embodiment, surrounded by an unbroken layer, or tube, of the beta titanium alloy. This layer of beta titanium alloy may have a substantially uniform thickness in one embodiment. The wire may have an outer diameter of between 0.001-0.01 inches. Other diameters may be used in other examples. Thereafter, an insulating layer may optionally be added depending on the application for the wire. For example, the wire may be dipped in liquefied ethylene tetrafluoroethylene (ETFE) which is then allowed to solidify. Alternatively, such an insulating layer may be applied using an extrusion process, such as a micro-extrusion application process. In a specific example, the final wire may have an outer diameter of between 0.002-0.005 inches, or about between 0.0035-0.005 inches. Such an embodiment may be well-suited for some coil applications. In another particular example, the final wire may have an outer diameter of between 0.0010 inches-0.0025 inches, which may be well-adapted for some cable embodiments.

The process discussed above provides a wire that may have a low-resistance core and may further include a layer that contacts and surrounds this core having a relatively low elastic modulus. In one example, the material forming the core may have a resistivity of less than 25 micro-ohm-cm (or between 10 micro-ohm-cm and 20 micro-ohm-cm in a more specific example) and the outer layer of material surrounding the core may have an elastic modulus of between 30 GPa and 90 GPa.

Replacing MP35N with beta titanium alloy results in a wire with superior qualities and that is better suited for medical device applications. A medical electrical lead carrying one or more MP35N wires will be significantly more stiff than one formed of wires made from a beta titanium alloy because of the relatively high elastic modulus for MP35N and because of the embrittlement of the MP35N resulting from having to anneal this alloy at a temperature lower than its optimal annealing temperature to prevent melting of the low-resistance core. The lead will therefore be more susceptible to repeated bending and flexing, as will likely occur in chronic implant scenarios. These factors may result in the need to replace the lead carrying the MP35N wires more often, subjecting the patient to the inconvenience of a medical procedure.

The properties of beta titanium alloys, including their high yield strength, allow these materials to be readily adapted for coil applications. As is known in the art, coils are formed by winding or gathering consecutive coil turns around a central axis. Generally, this winding or gathering is performed around a mandrel or other central structure that lies substantially along a central longitudinal axis of the coil. This mandrel is typically removed after the winding process is complete, leaving a central lumen that can be used, for instance, to receive a stylet, guide wire, or other guiding device.

Because beta titanium alloys exhibit a high yield strength as compared to MP35N, and further because these alloys have a very low ratio of elastic modulus/yield strength as compared to MP35N, the beta titanium wires are able to be used in coil configurations having a large coil pitch. As a result, the number of wires used to form the coil (that is, the number of filers in the coil) can be dramatically increased when beta titanium alloys are used. Moreover, for a coil having a given number of filars, the overall coil diameter can be decreased when a beta titanium alloy is used instead of MP35N to form the filars. This provides a device (e.g., a lead) with a smaller outer diameter. These advantages will be discussed further below.

Not only do beta titanium alloys result in superior coil configurations, but they also provide important benefits when cable configurations are required. As is known in the art, coils are formed by winding or gathering consecutive coil turns around a central axis. For instance, the winding or gathering may be performed around a mandrel in the manner previously mentioned. When the mandrel is removed after the winding process is complete, the coil defines a tube around the central axis which may be described as an "air core". If the coil is used within a medical lead, this tube may be used to receive another device such as a stylet.

In contrast to coils, cables are formed by twisting multiple parallel wires together. In this case, there is no central structure around which the wires are twisted and there is no "air core" defined by the twisted wires after the twisting process is complete. That is, the cable is a substantially solid structure defined by the twisted wires.

As in the case with coils, benefits exist for using beta titanium alloy wires, including those containing low-resistance cores, in the production of cable structures. After a cable is twisted in the manner described above, the multiple wires within the cable are under stress. As a result, when the force that was applied to accomplish the twisting is removed, the wires tend to "untwist" to return to their original parallel configuration. To allow the wires of the cable to remain "twisted together" after the cabling force is removed, the wires are heated to a stress-relieve temperature, which is the temperature at which the stress presented within the material is removed so that "untwisting" will not occur. Beta titanium alloys have a lower stress-relieve temperature than MP35N, simplifying the manufacturing process while conserving energy. Moreover, at stress-relieve temperatures, biocompatible beta titanium alloys will not become brittle, resulting in ductile cables that are able to tolerate a large amount of stress without cracking or breaking. In contrast, at its stress-relieve temperature, MP35N does become brittle.

The embrittlement issues associated with using MP35N wires in a cable are similar to issues discussed above in relation to annealing MP35N at temperatures that are too low. In particular, embrittled MP35N wires of a cable structure become more susceptible to repeated flexing, bending, and longitudinal force so that the lifetime of MP35N cables are shortened, possibly requiring explant of devices (e.g., leads) that carry such cables whereas a similar device carrying one or more beta titanium alloy cables would have a significantly longer lifetime. The use of beta titanium alloys in cable structures is discussed further below.

Another benefit to using beta titanium alloy wires such as those containing low-resistance cores relates to their low elastic modulus (E) which ranges from 30GPa to 90 Gpa. A more specific example selects a beta titanium alloy having an elastic modulus of between 50GPa to 90 Gpa. The various examples set forth above are included in one or more of these groups. For instance, Ti-15Mo has an elastic modulus of 80 GPa and TNTZ has a elastic modulus of 70 GPa. This is significantly lower than the elastic modulus for MP35N, which is 230 GPa. This results in beta titanium alloy coil and cable structures that are less susceptible to stress and strain than comparable structures made from MP35N, as shown in FIG. 5.

Figure 5:
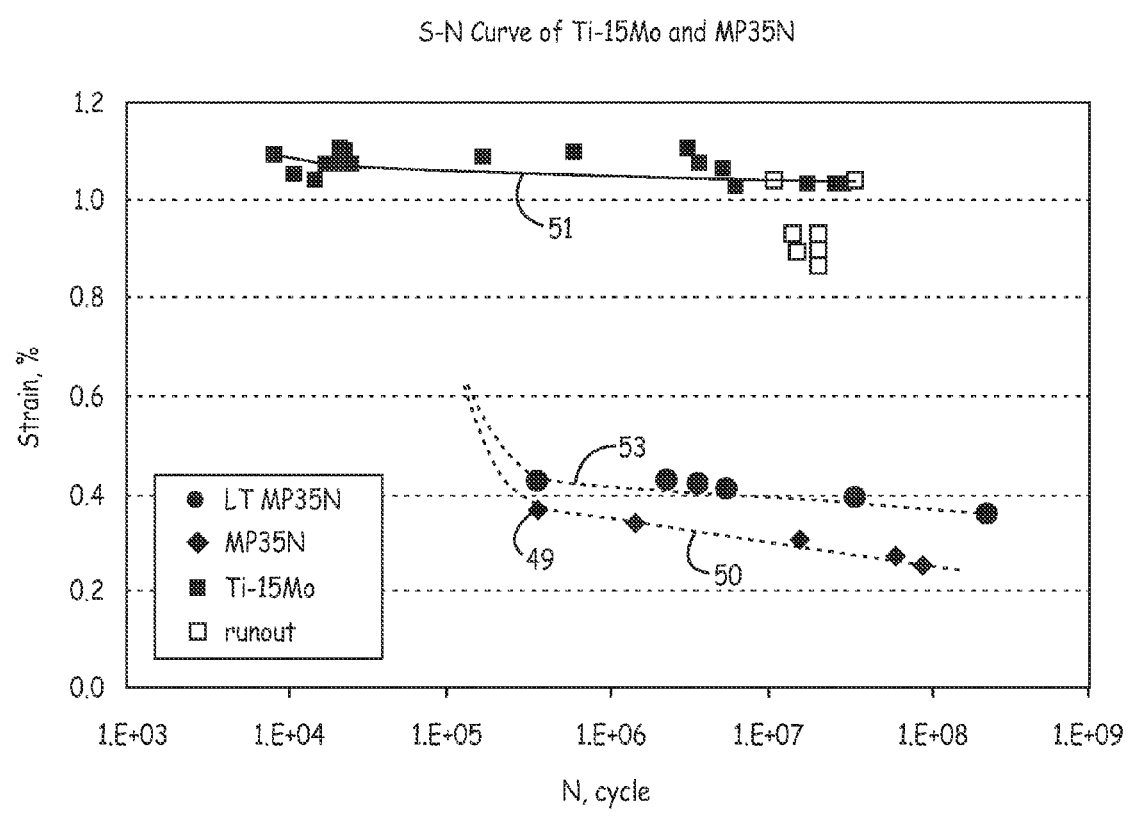
FIG. 5 is a diagram illustrating S-N curves for Ti-15Mo, MP35N and low-titanium MP35N (LT MP35N).

FIG. 5 is a diagram illustrating S-N curves for the beta titanium alloy Ti-15Mo as compared to MP35N and low-titanium MP35N (LT MP35N). During spin-fatigue testing, Ti-15Mo and MP35N wires having diameters of 0.004 inches were, during repeated cycles, subjected to strain (as a percent) shown along the y axis. The number of cycles (N) is represented along the x axis. The identified points along the curve indicate when failures occurred, although in some cases, testing was halted before the wires failed as indicated by the "runout" designators.

As may be appreciated from the data presented in FIG. 5, Ti-15Mo wires have a fatigue endurance limit that is about three times higher than that for MP35N. For instance, point 49 of curve 50 represents a strain of a little under 0.4%. At this level of strain, an MP35N wire experiences a failure after about 200,000 cycles. In contrast, at this level of strain, a Ti-15Mo wire has an infinite lifetime. Moreover, Ti-15Mo can undergo about three times the strain before a failure occurs, as shown by curve 51 corresponding to the collection of data for the Ti-15Mo failures. For the low-titanium MP35N wire, the results are similar to those of the MP34N wire, as indicated by comparing curves 50 and 53.

The data shown in FIG. 5 was obtained when testing wires that did not have low-resistance cores, but were instead wires of solid Ti-15Mo (for curve 51), solid MP35N (for curve 50), and solid LT MP35N (for curve 53). If the wires instead each included a low-resistance core of the same diameter and composition, (e.g., all silver cores having an area of 10% of the total cross-section), the curves would remain the same shape but would each "shift-upward" slightly, with the Ti-15Mo curve 51 shifting upward a little less than the other two curves 50 and 53. What is important to note is that regardless of whether a low-resistance core is provided, a given Ti-15Mo wire will be able to withstand about three times the amount strain as its MP35N or LT MP35N counterpart.

Another benefit of using a beta titanium alloy wire relates to the ability to "tune" the resistance of the wire to a desired value. In a wire having an outer layer formed of MP35N surrounding a low-resistance silver core, the resistivities of the core material and that of MP35N are grossly mismatched. That is, the silver has a resistivity of approximately 1 micro-ohm-cm whereas the MP35N has a resistivity of about 100 micro-ohm-cm. A predetermined length of the silver-cored MP35N wire can therefore be modeled as a first resistor having a resistance of 1× in parallel with a second resistor having a resistance of 100×. The overall resistance of this network is largely dictated by the silver core, with the resistance of the outer MP35N layer having very little effect on overall resistance.

However, if the core and the surrounding layer are formed of materials have resistivities that are closer to one another, the resistance of the wire can be "tuned" so that it approximates a desired value. For instance, the resistance of a predetermined length of wire (or a cable or coil formed of one or more such wires) can be tuned to match the resistance of one or more other structures such as a connecting electrode 36, a conducting electrode 38, or another sensor adapted to sense a signal from the body of patient (FIG. 3). As is known in the communication arts, matching of resistances in this manner will prevent signal reflections of the type that can obscure a sensed or a transmitted signal.

As one example of using materials that facilitate tuning, tantalum and niobium both have a resistivity of 15 micro-ohm-cm. Either one of these materials may be selected for use as the core while using a relatively lower-resistivity beta titanium alloy such as TNTZ having a resistivity of 90 micro-ohm-cm as the layer that directly surrounds this core. The overall resistance of such a wire can be tuned by adjusting the size of the diameter of the inner core as compared to the diameter of the overall wire. The resistance of a given length of wire can thereby be matched to the resistance of an electrically-conducting element (e.g., a conducting or connector electrode, etc.) to which it is to be coupled, thereby improving signal transmission and reception quality. This is discussed further below.

Another related benefit achieved from using biocompatible beta titanium alloy wires involves the fact that the various biocompatible beta titanium alloys exhibit a wide range of resistivities. Therefore a particular beta titanium alloy may be selected to provide a degree of resistivity required for a given application. Generally, it may be desirable to have wires with resistances that are as low as possible, since this will minimize power losses and allow drive circuitry that is transmitting/receiving signals in the cable or coil structures to be operated more efficiently.

Figure 8:
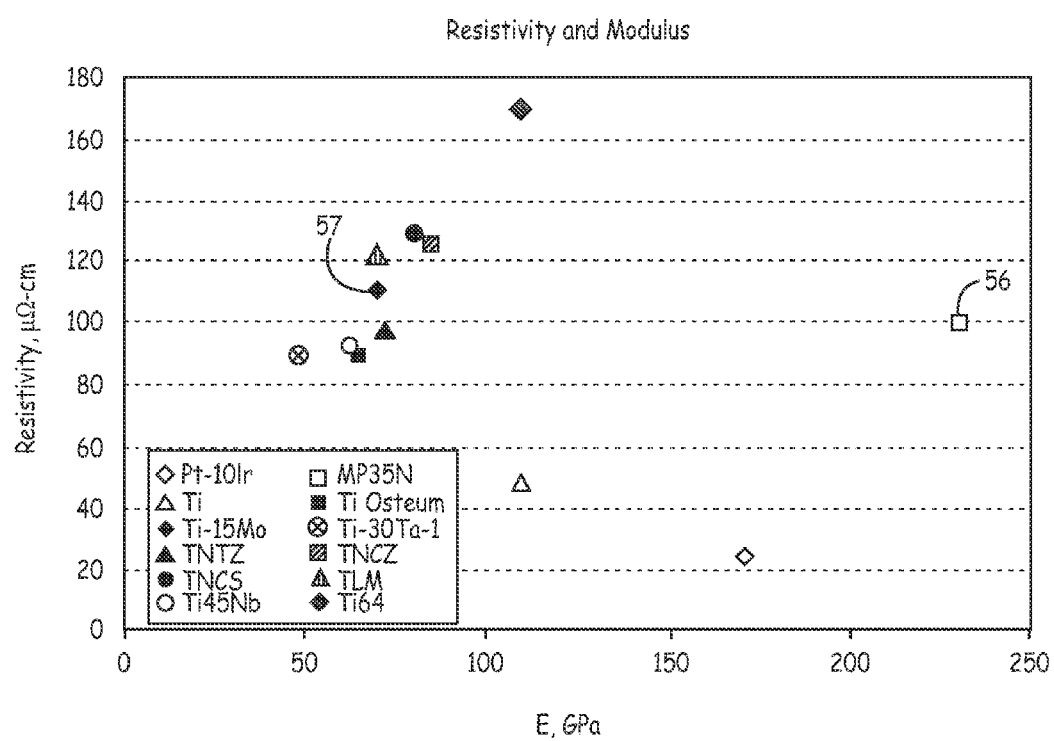
FIG. 8 is a diagram plotting resistivity against the elastic modulus (E) for various materials.

In contrast, high-resistivity materials can be better suited for use in magnetic resonance imaging (MRI) applications to reduce heating. For instance, consider a coil structure that is to be used in an MRI conditionally-safe lead. A magnetic field within the center of the coil can induce currents that should be limited to avoid heating. Therefore, in such a scenario, it is generally desirable to form the coil of wire that has a higher resistance to limit the induced currents flowing within the coil when the coil is subjected to a magnetic field. This cannot be readily achieved with MP35N wire having a silver core, since the silver has a very low resistivity. Rather, a higher resistance wire can be provided by instead selecting a beta titanium alloy such as Ti-15Mo, TLM, TNCZ or Ti-30Ta for use as the outer layer (such alloys having a higher resistivity than MP35N as shown in FIG. 8) with niobium or tantalum being selected as the core, since either material exhibits a significantly higher resistivity than silver. This can provide a coil that is better suited for use in MRI conditionally-safe applications. In some such applications, it may be desirable to eliminate the core entirely to further increase resistance of the wire. This will be discussed further below.

As is evident from the foregoing examples, in applications wherein wire resistance is an important factor in providing an acceptable solution, the wide range of resistivities that are exhibited by biocompatible beta titanium alloys makes it possible to select the right alloy to provide the desired solution. In some examples, use of a higher resistivity material (relative to silver) may be used for the core to further enhance performance. Such materials may include, for instance, niobium and tantalum and their respective alloys.

Figure 6:
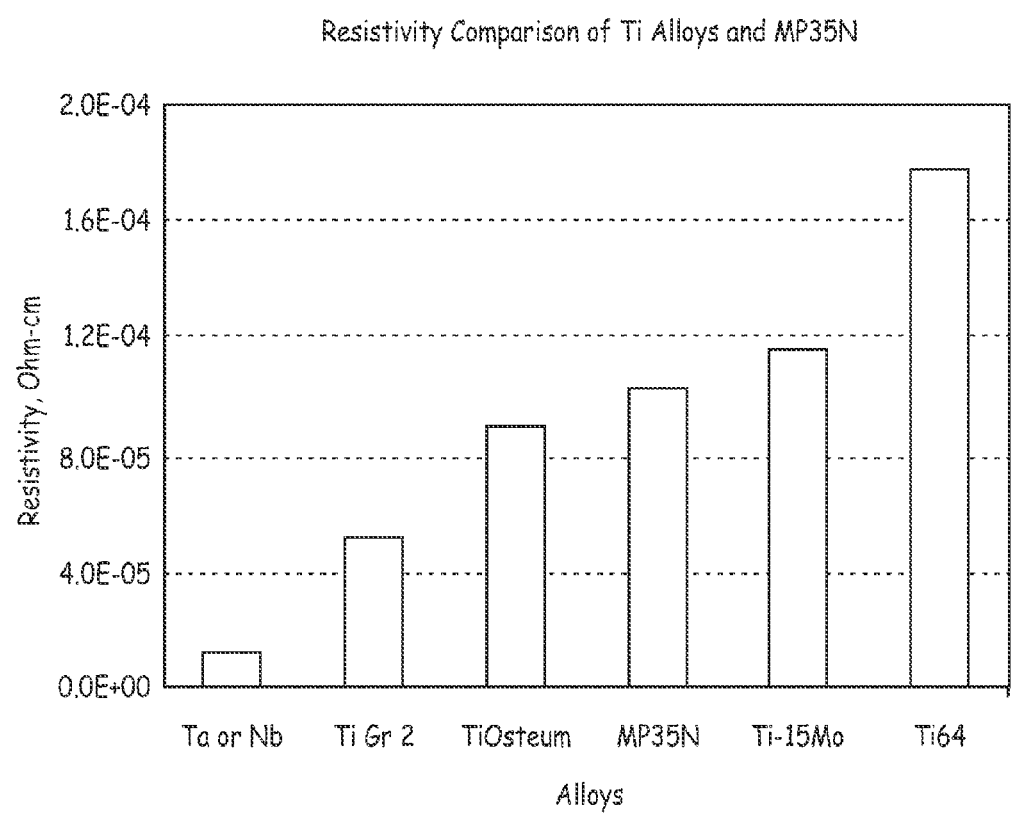
FIG. 6 is a graph illustrating resistivities of various alloys.

FIG. 6 is a graph illustrating resistivities (in ohm-cm) for various beta titanium alloys as well as for MP35N. As shown, MP35N has a resistivity of about $1.0 \times 10^{-4}$ ohm-cm, or about 100 micro-ohm-cm. A wide disparity exists between this resistivity and that of silver (not shown), which is about 1 micro-ohm-cm, making a MP35N wire having a silver core difficult to tune. In contrast, the resistivity of TiOsteum, is about $9.0 \times 10^{-5}$ ohm-cm, or 90 micro-ohm-cm and the resistivity of Ta is about $15 \times 10^{-5}$ ohm-cm, or 15 micro-ohm-cm. Because the resistivities of these two materials is closer to one another, a wire having a Ta core surrounded by an outer layer, or tube, of TiOsteum can be much more readily tuned than can an MP35N wire with a silver core.

FIG. 6 further shows the wide range of resistivities exhibited by various biocompatible beta titanium alloys. Thus, a beta titanium alloys having a desired resistivity is available for a wide variety of applications, such as those discussed above.

Figure 7:
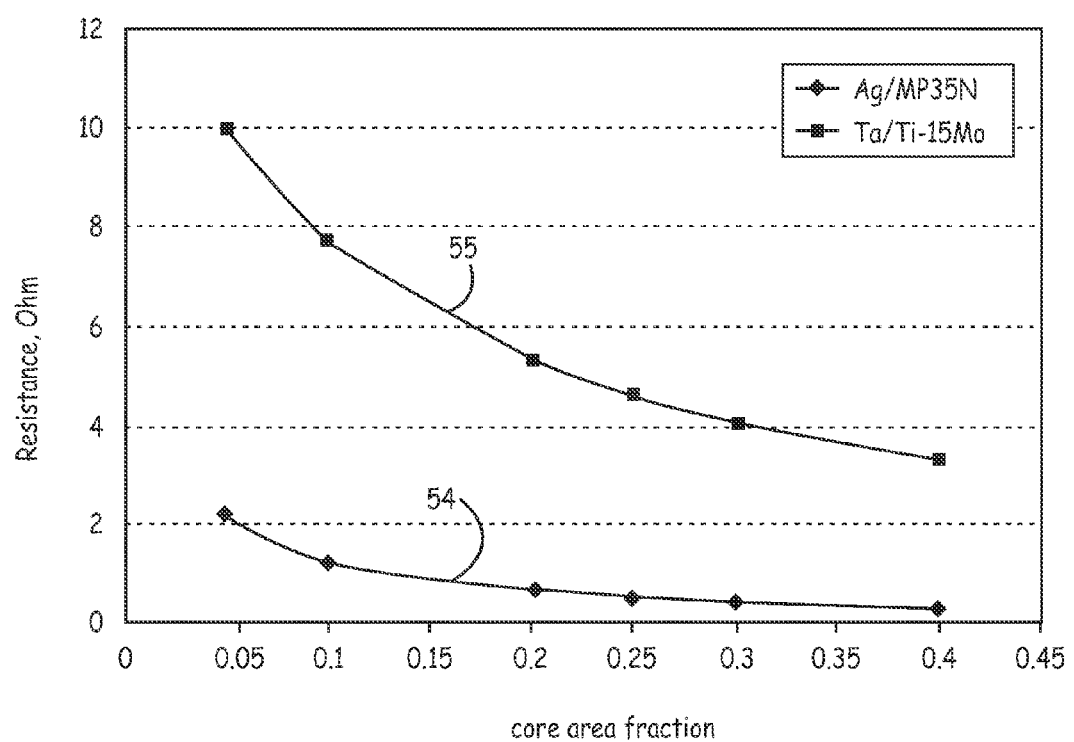
FIG. 7 is a graph illustrating tunability of resistance for a silver-cored MP35N wire as compared to that for a Ti-15Mo wire having a tantalum core.

FIG. 7 is a graph illustrating tunability of a silver-cored MP35N wire as compared to that for a Ti-15Mo wire having a tantalum core. Both wires are 10 cm (about 4 inches) in length and have a diameter of 0.004 inches. The fraction of the core area relative to the core area of the entire wire (i.e., the "core area fraction") is represented along the x axis. The resistance of the wire (in ohms) is indicated along the y axis. By increasing the core cross-sectional area relative to the cross-sectional area of the overall wire, the resistance of the wire will decrease. This effect is bounded. Specifically, if the ratio of core cross-sectional area to overall cross-sectional area is decreased below 0.05 (or about 5 percent) or increased above about 0.4 (or about 40 percent), the amount of change occurring because of a change in core area is minimal. Between the two limits, the resistance of the MP35N wire having the silver core will range between about 2 ohms to about 0.5 ohms, as shown by curve 54. For Ti-15Mo with a tantalum core, the wire can be tuned from about 3.5 ohms to about 10 ohms, as indicated by curve 55. This allows the beta titanium wire to be tuned over a significantly larger range for a much larger variety of applications. In other example wire configurations having outer layers formed of beta titanium alloys surrounding low-resistance cores, a range over which tuning may occur may generally be between 3 ohms to 15 ohms for a wire having a length of about 10 cm (or approximately 4 inches).

FIG. 8 is a diagram plotting resistivity against the elastic modulus (E) for various materials. The resistivity is illustrated along the y axis (in µohms-cm) and E is represented along the x axis (in GPa). As shown in this diagram, MP35N exhibits a much higher E at about 230 GPa than any of the beta titanium alloys, as illustrated by point 56. In particular, Ti-15Mo has an E of 80 GPa, as represented by point 57. This is almost one-third the E of 230 GPa for MP35N. Other beta titanium alloys have a similar elastic modulus. For instance, TiOsteum has an elastic modulus of about 70. The much higher elastic modulus for MP35N indicates that MP35N is much stiffer than beta titanium alloys, and MP35N is therefore able to undergo lower fatigue for a shorter period of time. As a result, medical devices containing wire (e.g., coil or cable structures) made of beta titanium alloys may have a much longer lifetime than devices carrying counterpart structures formed of MP35N. As a specific example, high strain may occur at a site at which a lead or other device experiences repeated bending at a given location, thereby causing fatigue. A lead implanted in a patient's torso may be subjected to such fatigue because the patient frequently bends at the waist, for instance. This may take a toll on the life of a device (e.g., lead) having an MP35N wire, necessitating explant sooner than if a corresponding beta titanium alloy device is used.

FIG. 8 further shows that MP35N has a higher resistivity than some of the beta titanium alloys. In particular, MP35N has a resistivity of about 1.0 E-04 ohm-cm, or about 100 micro-ohm-cm, as shown by designator 56. Other beta titanium alloys have a lower resistivity. For instance, Ti-30Ta-1 and TiOsteum each have a resistivity lower than that of MP35N at about 9.0E-05 ohm-cm, or about 90 micro-ohm-cm. Ti-30Ta-1 and TNTZ likewise have a resistivity lower than that of MP35N As a result, these beta titanium alloys present better tuning potential than the MP35N, since their resistivity is closer to that of any low-resistivity material employed for a core.

Conversely, if a high-resistivity material is desired for use in a particular application, such as a coil configuration to be used in an MRI-conditionally safe application, a beta titanium alloy like Ti-15Mo may be selected having a resistivity of about 110 micro-ohm-cm.

Other benefits relate to the biocompatibility of beta titanium alloys such as Ti-15Mo as compared to MP35N. This is shown in Table 2, which describes the metal ion release of MP35N and Ti-15Mo when submerged in saline for four weeks.

TABLE 2

| Ion Release ($\mu g/mm^2$) | MP35N | Ti—15Mo |
| --- | --- | --- |
| Ti | — | 0 |
| Mo | 0.00013 | 0.00018 |
| Co | 0.0022 | — |
| Ni | 0.0022 | — |
| Cr | 0.0000 | — |

As shown in Table 2, when submerged in saline solution, the total metal ion release occurring from MP35N is more than twenty-five times higher than for Ti-15Mo over a four-week period. The highest contributors to this ion release are Co and Ni, with release levels being 0.0022 $\mu g/mm.^2$ In general, this level of ion release is not exhibited by biocompatible beta titanium alloys. In particular, since biocompatible beta titanium alloys such as Ti-15Mo do not contain Co and Ni, the overall ion release is much more limited.

Furthermore, because Ti-15Mo and other beta titanium alloys do not contain Co, such alloys do not exhibit metal ion oxidation (MIO). MIO occurs when the Co contained by MP35N ionizes and infuses into the surrounding insulating layer 46 (e.g., polyurethane). This reduces the lifetime of the insulating layer, making it necessary to explant the device (e.g., the lead) sooner than would otherwise be required for a device that instead carries wires made of biocompatible beta titanium alloys such as Ti-15Mo which do not contain Co and thus do not exhibit MIO.

Figure 9:
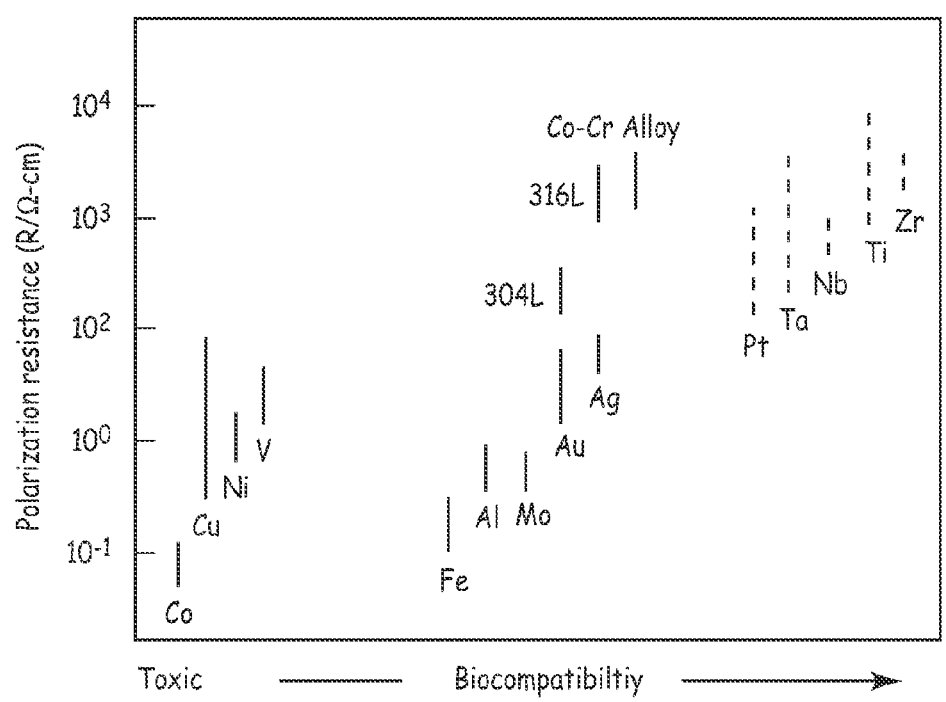
FIG. 9 is a graph of the level of biocompatibility of various elements as compared to polarization resistance.

FIG. 9 is a graph of the level of biocompatibility for various elements as compared to polarization resistance (N. Niionmi, *Journal of Metal*, June 1999, pp. 32-34). Biocompatibility is illustrated along the x axis. Polarization resistance (R/Ω-cm), which is generally inversely proportional to the corrosion rate, is shown along the y axis. Elements such as Ti, Mo, Nb, Ta, Zr, Cr, Fe, and Sn included in biocompatible beta titanium alloys exhibit superior biocompatibility as compared to elements Co and Ni of MP35N. This is particularly important where applications involving leads to be implanted within the brain are concerned. For instance, leads configured to deliver deep brain stimulation (DBS) therapy optimally are associated with a minimum level of ion release such as is exhibited by biocompatible beta titanium alloys of the type described herein.

Still another benefit of using beta titanium alloys rather than MP35N relates to price. This is shown by comparing costs of Ti-15Mo to MP35N. While the two are substantially the same price per pound, Ti-15Mo is much less dense than MP35N. Specifically, a cubic centimeter of Ti-15Mo weighs 4.95 grams versus 8.43 grams for the same volume of MP35N. As a result, it is estimated that for about a same amount of money, Ti-15Mo will produce about 70% more wire than MP35N.

Additionally, beta titanium alloys are weld-compatible with various materials typically included in implantable devices such as Nb, Nb alloys, Pt, Pt alloys, Ta and Ta alloys. This allows bonds to be readily created with such materials. In contrast, MP35N is not weld-compatible with these materials. As a result, it may take longer to form a good weld between a wire formed of MP35N and one of these materials. Additionally, more MP35N pieces may fail inspection.

Some of the various characteristics of Ti-15Mo and MP35N described above are summarized in the following Table 3:

TABLE 3

| Characteristic | MP35N | Ti—15Mo |
| --- | --- | --- |
| Metal Ion Release | >.0045 micrograms/$mm^2$ | .00018 micrograms/$mm^2$ |
| Biocompatibility | Ion Release of about 25X | Ion release of about X |
| Manufacturability | Weld-incompatible with Nb, Nb alloys, Pt, Pt alloys, Ta and Ta alloys | Weld-compatible with Nb, Nb alloys, Pt, Pt alloys, Ta and Ta alloys |
| Density | 8.43 grams/$cm^3$ | 4.95 grams/$cm^3$ |
| Length of Wire for a given cost | L | Approximately 1.7L |

The foregoing, and other benefits to be discussed below, are provided by using a biocompatible beta titanium alloy having an elastic modulus of between 30 GPa and 90 GPa to form wires to be used within medical devices including, but not limited to, leads or lead extensions. In some examples, these wires optionally have low-resistance cores. Such wires may be used in a variety of configurations, including coil configurations or cable arrangements, as will be discussed further below. For example, in FIG. 3, a single such wire may extend between each connector electrode 36 and a corresponding conductor electrode 38 such that the body of the device carries four wires, each being electrically insulated from the other wires so that independent signals may be carried by each wire. Alternatively, if redundancy is required, more than one wire may extend between each such connector and conductor electrode pair, with such wires being electrically coupled one to another. In this latter case, more than four wires may be carried by the lead body of FIG. 4 to provide connectivity between the four connector and conducting electrode pairs 36, 38. Within the lead body, the multiple wires may be twisted together in a cable arrangement or may instead comprise a coil. The various embodiments are discussed further below.

Returning now to FIG. 4B, this figure illustrates a side cutaway view of a distal end of a lead 47 that carries a beta titanium wire having a low-resistance core 40 as described herein electrically and mechanically coupled to an electrode 43. Lead 47 is shown to carry a single wire 39 having a low-resistance core 40 surrounded by tube 42 which may be formed according to methods described herein. To affix an end of wire 39 to an inner surface of electrode 43 (also shown cut-away), the end of the wire may be abutted to the inner surface of the electrode 43 and the tube 42 may be heated to create an electrical bond with the inner electrode surface. In one embodiment, one or more conductive joints 45 may be formed on one or more sides of tube 42 to facilitate this bonding, as by melting one or more beads of material having a high conductivity.

Within the lead body, wire 39 may extend substantially the length of lead body to electrically and mechanically couple to a connector electrode 36, such electrode being adapted to interface with a connector of an implantable device such as IMD 12.

Lead 47 may carry only a single conducting electrode 43 that is coupled to a corresponding connector electrode (not shown in FIG. 4B) via wire 39. Alternatively, lead may carry additional conducting electrodes, each in a manner similar to that shown in FIG. 3, with each conducting electrode being coupled to a corresponding connector electrode 36 via an associated wires in some embodiments. Each such wire may have a core formed of a low-resistivity material encased by a layer of beta titanium alloy, as previously disclosed. As is possible with the beta titanium alloy, each such wire may have a resistance that is tuned to a corresponding structure to which it is connected. For instance, in FIG. 4B, the resistance of wire 39 may be tuned to that of electrode 43. In a more specific example, electrode 43 has a same, or similar resistance as a corresponding connector electrode located at a proximal end of lead such that the resistance of wire 39 is tuned to both of these interconnecting structures.

As discussed above, multiple wires of the type described herein may be configured in either a coil or a cable arrangement. When configured in either configuration, the beta titanium alloy wires provide significant benefits as compared to low-resistance core wires that are instead formed of MP35N, as has traditionally been the case. The following discussion will therefore specifically consider examples of beta titanium alloy wires arranged in coil configurations. Thereafter, cable configurations will be described.

Figure 10A:
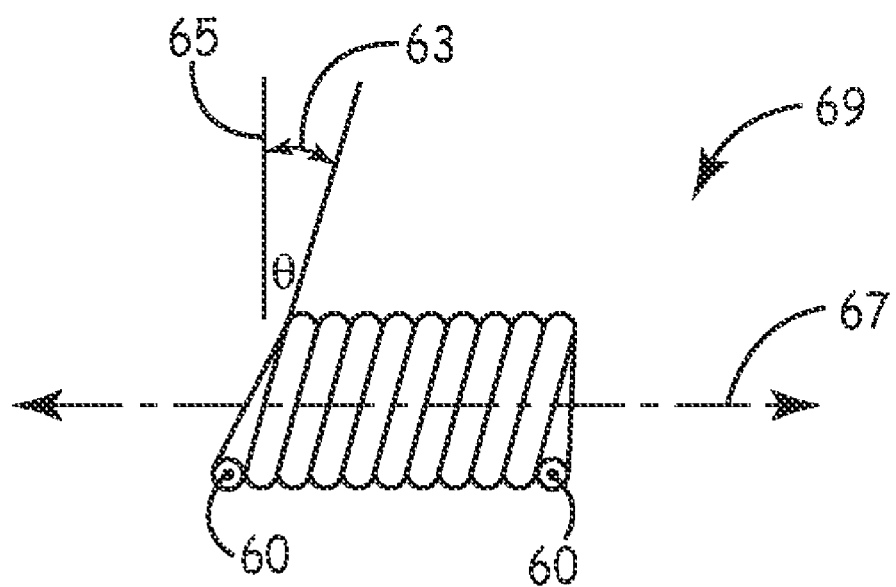
FIG. 10A is a side view of one embodiment of a coil formed of at least one filar having a beta titanium outer layer and a low-resistance core.

FIG. 10A is a side view of one embodiment of a coil 69 that is formed of at least one filar 60 (or wire) of the type described herein having a beta titanium outer layer and a low-resistance core. For purposes of FIG. 10A, it will be assumed one wire is being wound to form the single-filar coil, although more filars may be used as discussed in reference to FIG. 10B or 10C.

In one embodiment, it is desirable to have a filar that is as thin as possible for use in coil 69 since a coil formed of a small diameter filar will withstand more bend stress than one formed of the same material but which has a larger diameter.

A filar suitable for coil 69 can be obtained by an iterative process that draws the wire comprising beta titanium tube 42 and a low-resistance core 40 (FIG. 4A) through a die, followed by an annealing process to anneal the beta titanium tube. In one example, this annealing will occur at between 600-900° C. for beta titanium alloys. In particular, for Ti-15Mo, the annealing temperature is about 730° C. At these temperatures, the beta titanium will be completely annealed and will not become brittle. This process may be repeated multiple times to obtain a filar of the desired diameter.

The wire may have a starting inner diameter ranging from 0.1 inches to 2 inches (or between about 0.25 cm-5.0 cm). A low-resistance core may be inserted into the tube, with the core being formed of a material having a resistivity of less than 25 micro-ohm-cm. Following the iterative drawing and annealing steps, the diameter of the wire may be between about 0.001 inches and 0.01 inches. In a more specific example, the ending diameter of the filar may be between about 0.001 inches and 0.002 inches. In a still more specific example, this diameter is about 0.0013 inches.

As discussed above, one advantage with using the biocompatible beta titanium alloy wire as opposed to an MP35N wire is that MP35N must be annealed at temperatures above 1000° C. to prevent brittleness. However, at this temperature, the low-resistance core 40 will melt, causing manufacturing challenges. This is not an issue for a low-resistance core beta titanium alloy wire, since this wire may be fully annealed below the melting temperature of the core and the resulting wire will not be brittle following the annealing process.

As shown in FIG. 10A, after being drawn to a desired diameter, filar 60 may be wound to form a coil. As defined herein, and as known in the art, a "coil" refers to a series of multiple connected turns formed about a central axis 67 by gathering or winding. This is opposed to a cable structure that is formed by twisting multiple substantially parallel wires together to form a rope-like configuration.

During a coil winding process, filar 60 may be wound around a mandrel (not shown in FIG. 10A) which is removed after the winding process is complete. The filar 60 is wound at a desired pitch angle $\theta 63$ that may be measured with respect to a cross-sectional axis 65 that is perpendicular to the longitudinal axis 67 of coil 69.

When the pitch angle $\theta 63$ is selected to be zero such that the coil windings are substantially parallel to cross-sectional axis 65, conductor coil 69 is able to withstand a high level of stress. In this case, when force is exerted on filar 60, conductor coil 69 is readily able to expand a maximum amount without breaking or becoming permanently deformed.

However, disadvantages exist to having a smaller pitch angle. For instance, the amount of material required to form coil 69 increases as pitch angle $\theta 63$ decreases. As a result, the total weight and overall resistance will increase with the decreasing pitch angle. The increasing resistance will, in turn, result in higher power losses over the length of the coil. Moreover, outer diameter will increase as the pitch angle $\theta 63$ decreases.

While selecting a pitch angle $\theta 63$ that is somewhat above zero will decrease material costs and weight of the product while reducing power losses and outer diameter, selecting a pitch angle that is too large will increase manufacturing complexity. This is particularly true when coil 69 is formed of a single filar 60 as shown in FIG. 10A (rather than of multiple filars as will be described in reference to FIG. 10B). When coil 69 is formed of a single filar, it is difficult to maintain the single filar at an angle that is above about 30° during the winding process. To achieve a greater pitch angle in a single-filar embodiment, a special winding mechanism must be used that increases production costs. Therefore, attempting to increase the pitch angle too much to save material costs will have the adverse effect of increasing manufacturing complexity. For this reason, when coil 69 is formed of a single filament, it is desired in some examples to select pitch angle $\theta 63$ to be between zero and 30 degrees.

As mentioned above, in some embodiments, more than one conductor filament is used to form coil 69. This may be desirable, for example, in a lead having multiple conducting electrodes. In such a case, a coil having multiple filars that are each insulated one from another may be employed to electrically couple the multiple conducting/connector electrode pairs of the lead. That is, each conducting electrode 38 may be coupled to a respective filar that carries an outer insulating layer 46, as discussed in reference to FIG. 4A. The multiple filars may be wound into a single coil structure, as described in reference to FIG. 10B.

Figure 10B:
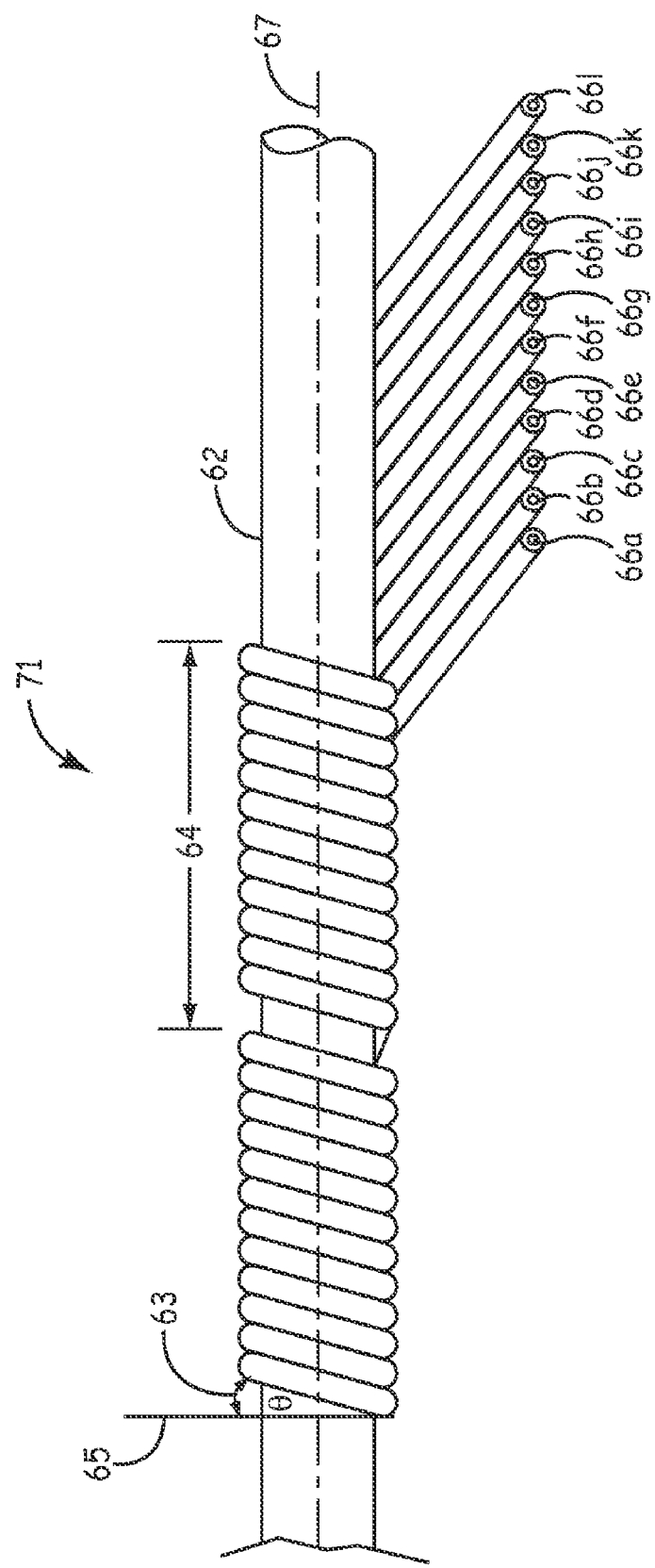
FIG. 10B is a side view of a coil according to another embodiment of the current disclosure.

FIG. 10B is a side view of a coil 71 according to another embodiment of the current disclosure. In this example, coil 71 is being wound of twelve filars 66a-66l, although more or fewer filars may be used in the alternative. In one embodiment, each of the twelve filars has substantially the same outer diameter, which may be between about 0.001 inches-0.01 inches. In a more specific example, the wires are between about 0.0035 inches-0.005 inches. Each filar may be formed by cold drawing, then annealing, a beta titanium tube surrounding a low-resistance core in a manner similar to that described above. While not shown in FIG. 10B, in one embodiment, each of filars 66a-66l includes an insulating layer 46 (FIG. 4A) so that each filar is insulated from adjacent filars and may independently transmit and receive signals.

The filars may be positioned side-by-side and coiled at a same time, as shown in FIG. 10B. Winding all filars at once in this manner is preferable because it saves time and helps maintain alignment. While the filars may instead be wound one at a time, the winding process would take longer to complete, and the spacing of the filars would be more difficult to control, adding complexity to the process.

In this example, the filars are being wound around a mandrel 62 that provides structure to maintain the shape of coil 71 during the winding process. Mandrel 62 may be removed upon completion of the winding, leaving an "air-core" coil. The center of the coil defines a space that may, for instance, receive a stylet or guide wire to aid in placing a device (e.g., a lead) that carries coil 71 at a desired location within a patient's body.

As is the case with the embodiment of FIG. 10A, filars 66a-66l may be wound at a pitch angle $\theta 63$ measured from cross-sectional axis 65. In general, as the number of filars increases, both the pitch angle $\theta 63$ and the pitch 64 must increase, wherein the pitch is the distance between adjacent turns of the same filar. Both the pitch angle $\theta 63$ and the pitch 64 is limited by the flexibility of the filar. Wires made of materials having a higher elastic modulus such as MP35N cannot accommodate as large of a pitch angle or pitch as those formed of beta titanium alloys having a much lower elastic modulus. Thus, coils of a predetermined diameter that are formed of MP35N wire cannot contain as many filars as those of a same diameter that are formed of beta titanium wire. Therefore, coils of a predetermined diameter that are formed of MP35N cannot provide as many electrical connections and are able to accommodate fewer electrodes when compared to a similar coil formed of beta titanium alloys.

The foregoing may be stated another way: a coil formed of the stiffer MP35N wires having a predetermined number of filars will require a larger diameter than a coil formed of beta titanium alloy having the same number of wires. For instance, if coil 71 is formed of eight MP35N wires, an outer diameter that is greater than 0.032 inches must be obtained if the pitch is to be limited to that which will not place undue strain on the wires. In contrast, if coil 71 is instead formed of eight beta titanium alloy wires, a coil having an outer diameter of about 0.016 inches, half that of the MP35N coil, can be obtained. Minimizing the size of a coil may allow the size of an associated device (e.g., a lead carrying the coil) to be substantially reduced, something that is very important for medical device applications. These considerations are discussed further in regards to FIG. 11A below.

Still another benefit of using a beta titanium wire to form coil 69, 71 involves the bend radius at yield that can be achieved by this coil as compared to a coil of similar dimensions formed of MP35N wire. The bend radius at yield measures the minimum radius that can be achieved by the coil without kinking or damaging the coil. Because a beta titanium alloy wire used to form the coil has a much lower elastic modulus, the resulting coil structure is not as stiff and has a smaller bend radius at yield than a similar MP35N coil. Therefore, a medical device such as a lead, lead extension, stylet, guide wire, or any other type of device that carries such a coil will likewise not be as stiff, and will be able to much more readily navigate the twists and turns of the human anatomy. A comparison of the bend radius at yield of an MP35N coil as opposed to that for a beta titanium alloy coil is provided below in reference to FIG. 11A.

FIG. 10C is a conceptual drawing of a side cut-away view of a coil containing eight filars 80a-80h ("filars 80"), each coupled to a respective one of ring electrodes 82a-82h ("electrodes 82", shown in cross-section in FIG. 10C), wherein the electrodes are carried by a distal end of a medical electrical lead 78. For instance, filar 80a is shown coupled to electrode 82a, filar 80b is shown coupled to electrode 82b, and so on. Each of the filars may be formed of a beta titanium alloy having a low-resistance core as described herein. The relatively large number of filars carried by the coil is made possible by the relatively large pitch and large pitch angle $\theta$ that is afforded by these filars, something not achievable when using conventional MP35N filars.

In one example, each of filars 80a-80h is provided with an insulating layer 46 (FIG. 4A) that insulates it from adjacent filars, thereby allowing each filar to carry an independent electrical signal. As discussed above, the insulating layer may be a polymer jacket or a layer formed of some other insulating material. Moreover, lead 78 may include an insulating lead body 83. This may be formed of any of the biocompatible polymer materials suitable for medical electrical leads, as described herein.

According to one example, lead 78 has a proximal end (not shown) carrying eight connector electrodes each similar to electrodes 36 of FIG. 3, and each being coupled via a respective one of filars 80a-80h to a corresponding one of conducting electrodes 82a-82h. These conducting electrodes may be electrically and mechanically coupled via a respective connecting electrode to corresponding connectors within a header of IMD 12. The IMD may thereby transmit signals to a patient to deliver therapy and/or to receive signals sensed from the patient for monitoring and diagnostic purposes, for example.

IMD 12 may contain a stimulation pulse generator that may be capable of delivering stimulation simultaneously via eight separate stimulation channels so that each of conducting electrodes 82a-82h provides an independent stimulation signal to patient 10 at a same time. In another scenario, IMD 12 may drive electrodes 82a-82h in a time-multiplexed manner such that not all of electrodes 82a-82h are being driven simultaneously. In still another example, IMD 12 may drive only a selected subset of electrodes 82a-82h, that subset being selected based on patient response or some other indication of a level of efficacy of therapy, level of paresthesia, and/or level of side effects resulting from stimulation via that electrode combination. Alternatively, multiple electrodes may be driven with a same signal. In yet another example, some of the electrodes 82 may be used to deliver signals to tissue of patient 10 while other electrodes 82 may instead sense signals. As yet another example, all or a subset of all, of electrodes 82 may be used to deliver stimulation some of the time while sensing signals at other times in a time-multiplexed manner. Such control options may depend on the stimulation and sensing capabilities provided by an IMD 12, which may be therapy dependent. In any event, lead 78 carrying the improved coil comprising filars 80 provides enhanced capabilities to deliver and/or sense more signals to/from more locations.

As previously described, filars 80 may each have a resistance that is tuned to that of electrodes 82 in the manner described above. In one example, not all electrodes 82 need have the same resistance, and the filars may have a resistance tuned to the electrodes to which they are coupled such that not all filars have a same resistance in one example.

It will be understood that FIG. 10C is a conceptual drawing that is not necessarily to scale. For instance, the ring electrodes may be substantially wider than a diameter of a single filar, as shown. What is important to note is that one or more filars may each be electrically and mechanically coupled to a respective electrode. This may be accomplished by removing a portion of an insulating layer that surrounds each of the filars to expose a portion of that filar (e.g., exposing an end of filar 80a). In one example, the exposed end of the filar may be abutted next to an inner surface of a respective conducting electrode (e.g., electrode 82a). This exposed portion of the filar may be heated by a resistive-, spot-, or a laser-welding process. This will bond the exposed portion of the filar to this surface of the electrode, forming an electrical and mechanical connection. This bonding may be further strengthened by melting beads of a fusible metal alloy to form electrically conductive joints 86. For instance, beads of a high-conductivity material may be melted to form these conductive joints. As previously noted, this can be accomplished more readily with the beta titanium wire because this wire is weld-compatible with various materials typically included in implantable devices such as Nb, Nb alloys, Pt, Pt alloys, Ta and Ta alloys. Similar bonds may be created with other interconnecting structures such as connector electrodes and/or sensors.

In other embodiments, the bond between a filar and a corresponding interconnecting structure (e.g., an electrode or sensor) may be created in another way. For instance, a mechanical coupling mechanism may be used instead of, or in addition to, a weld process. Such a mechanical coupling may involve crimping, pinching, threading, tying, or otherwise mechanically affixing a portion of the wire to the interconnecting structure to form a mechanical and electrical connection.

FIG. 10C shows each of electrodes 82 being coupled to a different respective one of filars 80. This may be desirable in an embodiment wherein a large number of such conducting electrodes are being coupled to connecting electrodes at a proximal end of the lead. In such a case, each of filars may be electrically insulated from the other filars to allow the conducting electrodes to be transmitting signals independently of the other electrodes, if desired. In this case, redundancy may not be possible since all of the available wires are needed to accommodate the multiple conducting electrodes. In another example, two or more filars may be coupled to a same electrode 82 to provide redundancy.

The lead of FIG. 10C may take many embodiments. For instance, electrodes 82 need not be ring electrodes but could be segmented electrodes that do not extend around the entire circumference of lead 78 such as shown in FIG. 3B and that optionally have a complex array geometry. Examples of complex array geometries are described in commonly-assigned application Ser. No. 11/591,188 filed Oct. 31, 2006 entitled "Programming Interface with a Cross-Sectional View of a Stimulation Lead with Complex Electrode Array Geometry", the entire content of which is incorporated herein by reference. Such geometries include electrodes occupying a same longitudinal position on a lead (such as shown in cross-section in FIG. 3B) as well as electrodes occupying different longitudinal positions on the lead. Additionally or alternatively, one or more sensors may be carried by lead 78, each being coupled to one or more of filars 80. Such sensors could include any of the sensors known in the art, such as pressure transducers, temperature sensors, sensors for measuring a level of a substance within the patient's body, motion and/or activity sensors, and so on.

As previously described, during the manufacturing process, filars 80 may be coiled around a mandrel 62 (FIG. 10B) which is removed after winding is completed, with the inner coil diameter defining an inner lumen. In an alternative example, filars 80 may be coiled around a structure that defines an inner lumen and which is not removed after winding. In either case, such a lumen may accommodate a stylet, guide wire, or another steering device that may be used to position the coil at a desired location within a patient's body.

While FIG. 10C illustrates eight conducting electrodes 82, each being coupled to a different respective one of the multiple filars 80 of the coil 78, it will be appreciated that a similar coil having a different number of filars may be configured in a similar manner. For instance, the twelve-filar coil 71 of FIG. 10B may be used to couple twelve conducting electrodes each to a respectively different connector electrode if desired so that twelve signals may be transmitted and/or received simultaneously (assuming that capability is provided by IMD 12). In another embodiment, even more than twelve filars may be provided.

The following Table 4 compares characteristics of an eight-filar coil formed of MP35N as compared to an eight-filar coil formed of a beta titanium alloy Ti-15Mo.

TABLE 4

Characteristics for Eight-Filar Coils

| Characteristic | MP35N eight-filar coil | Ti—15Mo eight-filar coil |
| --- | --- | --- |
| Fatigue life at strain of .38% | 200,000 cycles | Infinite |
| Pitch (with same OD) | X | 2X |
| Pitch Angle | Limited range | Wider range due to high stress tolerance |
| Coil Outer Diameter | At least 2D | D |

Table 4 shows that the fatigue life of a MP35N coil (assuming filars that are 0.004 inches in diameter) at a strain of about 0.38% is 200,000 cycles. In contrast, at this same strain, the Ti-15Mo coil has an infinite fatigue life. As such, an MP35N coil experiencing this strain will need to be replaced after a predetermined period of time, whereas this will not be necessary for a similar Ti-15Mo coil. Leads or other medical devices therefore have a longer implant life when a Ti-15Mo coil is used.

The fatigue data of Table 4 represents coils formed of filars without low-resistance cores. However, a similar comparison may be drawn between MP35N coils and Ti-15Mo coils if each are formed of filars having low-resistance cores. In particular, an MP35N coil formed of filars having low-resistance cores may tolerate somewhat more strain at 200,000 cycles than an MP35N coil formed of filars without a core. However, this additional strain tolerance will likewise be manifested in the Ti-15Mo coil formed of filars having low-resistance cores so that the difference in performance between the two coils remains the same.

Table 4 further compares the pitch of the two coils assuming an outer coil diameter that is the same. As discussed above in reference to FIG. 10B, the pitch describes the distance that may be obtained between adjacent turns of a same wire within a coil structure, as indicated by arrow 64. Pitch is affected by the strain tolerance of the material, as illustrated in FIG. 5. Beta titanium alloys are much more strain tolerant than MP35N. In particular, beta titanium alloys have a higher endurance limit such that they may be subjected to a relatively large amount of strain without permanently deforming or breaking. This is further quantified by their very low ratio of elastic modulus/yield strength, which is a characteristic required for forming multiple-filar high-pitch coils. Because of these characteristics, the pitch of the beta titanium alloy coils can be significantly increased over their MP35N coil counterparts. For instance, as shown in Table 4, the maximum pitch of an eight-filar MP35N coil having a given diameter will be about half the pitch that can be achieved for the eight-filar Ti-15Mo coil. This increased pitch allows the Ti-15Mo coil to include more filars than an MP35N coil having the same diameter.

Next, pitch angle is considered for both the MP35N coil and its Ti-15Mo counterpart. As previously discussed, the pitch angle θ63 (FIG. 10B) describes the angle between the coil filars and an axis perpendicular to the longitudinal axis of this coil, also referred to as the "cross-sectional axis". As shown, an MP35N coil has a limited pitch angle range. The pitch range is increased for Ti-15Mo coils, since they have a higher stress tolerance. As the pitch angle θ63 increases, more filars may be accommodated by a coil of a predetermined diameter. Stated another way, an MP35N coil having a same number of filars as a Ti-15Mo coil will have a much larger diameter than the Ti-15Mo coil. This is true, at least in part, because the pitch angle for the MP35N coil must be smaller than that for a Ti-15Mo coil. For instance, as previously discussed, while the outer diameter of an MP35N coil having eight filars is greater than 0.032 inches, the outer diameter of the Ti-15Mo coil that also comprises eight filars can be reduced to 0.016 inches. This is a significant size reduction which can provide important benefits for medical electrical leads and other devices that optimally have as small a diameter as possible to aid in device placement, increased patient comfort, and enhanced cosmetic appeal.

In addition to the benefits shown in Table 4, other benefits exist for using beta titanium alloy filars in coil designs. As previously discussed above, Ti-15Mo coils are easier to manufacture than the MP35N counterparts for several reasons. First, in the embodiment wherein the Ti-15Mo wires have a low-resistance core, a full annealing process can be performed for the Ti-15Mo filars since the annealing temperature is lower than the melting point of the materials which may be selected for the lower resistivity core. Because the Ti-15Mo wire can be fully annealed without risk of melting the core, the resulting coil structure will not be brittle. This is not the case for MP35N coils formed of filars having a low-resistance core. Because the MP35N filars must be annealed at a lower-than-desired annealing temperature to prevent melting of the core, the resulting filar (and hence the coil) is brittle and cannot withstand the same amount of fatigue as its biocompatible beta titanium alloy counterpart. Thus, coils that include MP35N filars are not as flexible and do not withstand the same amount of fatigue as the beta titanium alloy coils.

Figure 11A:
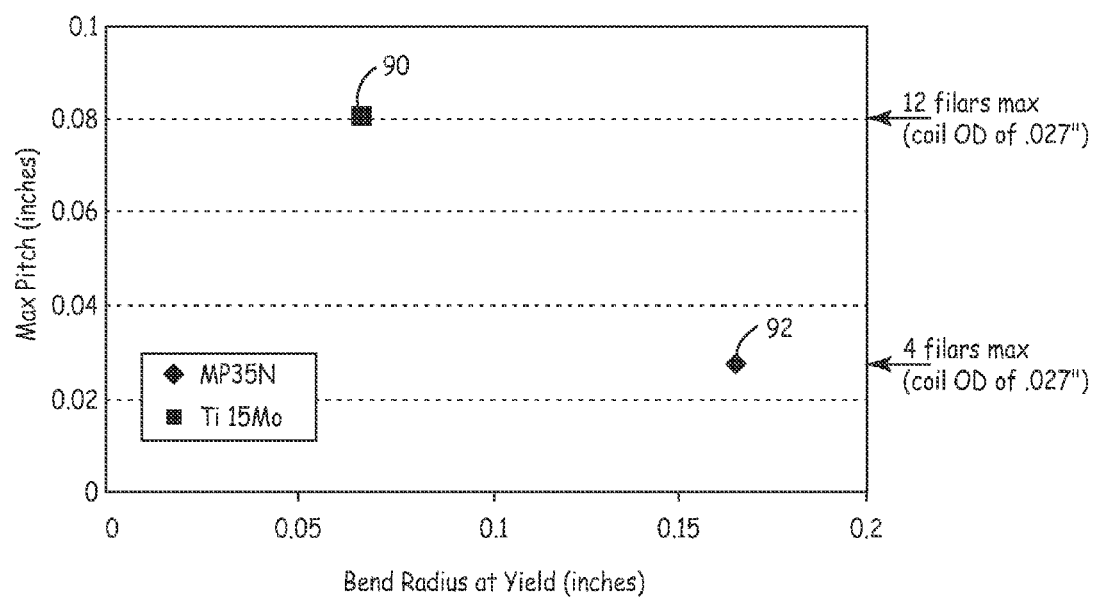
FIG. 11A is a graph comparing the bend radius to the maximum pitch for a first coil formed of Ti-15Mo and a second coil formed of MP35N.

FIG. 11A is a graph comparing the bend radius at yield of two coils (described in inches along the x axis) to the maximum pitch of the coils (represented in inches along the y axis.) In this example, each of the two coils has an outer diameter of 0.027 inches, with the filars of each of the coils having a diameter of 0.004 inches. Point 90 represents a coil formed of one or more Ti-15Mo filars having a maximum pitch of 0.08 inches when the bend radius at yield is about 0.067 inches. At this pitch, up to twelve filars can be included in the coil. Each such filar may be individually insulated such that up to twelve conducting/connector electrode pairs can be individually and independently interconnected using this coil. That is, twelve independent signals may be transmitted and/or received at once using this coil. In contrast, point 92 represents a coil formed of up to four MP35N filars. The filars of this coil have, at most, a pitch of about 0.027 inches when the bend radius at yield is about 0.0167 inches. At this pitch, only four filars, at most, can be accommodated. In other words, assuming each filar is individually insulated one from another, this coil can carry, at most, four independent signals, which would support only four conducting/connector electrode pairs.

While FIG. 11A applies specifically to a coil having an outer diameter of 0.027 inches, the results of FIG. 11A can be generalized in some respects. This generalization can be drawn by determining the ratio of maximum pitch to the coil outer diameter. For MP35N, the maximum pitch is about 0.027 inches, as indicated by point 92, resulting in a ratio of maximum pitch to outer diameter of 1. For MP35N, when this ratio exceeds 1, the strain increases significantly, resulting in a structure that will have a significantly shorter lifespan.

A similar ratio of maximum pitch to coil outer diameter may be approximated for Ti-15Mo. In particular, the ratio of maximum pitch to outer diameter is 2.96 (very close to three). Thus, the Ti-15Mo coil can include significantly more filars (2 to 3 times as many) for a given coil diameter, or conversely may have a much smaller diameter (2 to 3 times smaller) for the same number of filars as compared to its MP35N coil counterpart. These performance benefits can be provided for up to the number of filars (twelve in this example) represented by point 90 of FIG. 11A before the strain will increase significantly for the Ti-15Mo coil.

In implantable medical device applications, providing a device (e.g., a lead) that has a diameter that is as small as possible while providing for transmission of as many signals as possible is highly desirable. Moreover, it is beneficial to provide these characteristics without an increased strain which will shorten the lifespan of a device. As can be seen by the data of FIG. 11A, beta titanium alloys such as Ti-15Mo coils can provide for both of these objectives, supporting both a large filar count while minimizing outer diameter up to the illustrated limits and providing a smaller bend radius at yield. These objectives cannot be as readily achieved with MP35N coils.

Next, the bend radius at yield for MP35N coils and Ti-15Mo coils can be considered in more detail. As shown with respect to point 90, at a pitch of 0.08 inches, a Ti-15Mo coil having up to twelve filars can achieve a bend radius of about 0.067 inches at yield (that is, before permanent deformation of the coil occurs.) Thus, even when the pitch is high, a very small bend radius can be achieved by a coil comprising up to twelve Ti-15Mo filars. In contrast, point 92 represents a coil formed of only, at most, four MP35N filars, although the coil could contain fewer filars. At yield, the MP35N coil can only achieve a bend radius of 0.167 inches when the filars are coiled at a pitch of about 0.027 inches. Thus, the beta titanium coil has a bend radius at yield that is about 2.5 times smaller than that of the MP35N coil of the same 0.027 inch outer diameter. This is true even though the beta titanium coil has up to three times the number of filars. Because of the low modulus of the beta titanium alloy, the Ti-15Mo coil is less stiff and can undergo more flexing without permanent deformation than can the MP35N coil. The overall result is that the Ti-15Mo coil is smaller and more flexible, allowing it to more readily navigate through the tortuous paths of the human body during device placement (e.g., when a lead is being navigated into position in association with a therapy target.)

Point 90 represents the maximum pitch and minimum bend radius at yield that can be achieved by a Ti-15Mo coil having an outer diameter of 0.027 inches. It may be noted that a Ti-15Mo coil having this diameter can support any bend radius down to 0.067 inches and any pitch up 0.08 inches for a coil having up to twelve filars. Moreover, any number of filars fewer than twelve may be included in a Ti-15Mo coil having this outer diameter and such a coil will likewise be able to achieve a bend radius of 0.067 inches with a pitch of 0.08 inches. As discussed above, each filar of such a coil may be individually insulated from other filars to carry an independent signal.

In one example, a four-filar coil formed of a beta titanium alloy may have a pitch of up to 0.08 inches with an outer diameter of 0.027 inches. At this pitch and with only four filars, adjacent turns of the filars will not be touching one another in the manner shown in FIG. 10B. Instead, "gaps" will exist between a turn of one filar and an adjacent turn of another filar. One benefit of using this type of high-pitch configuration wherein adjacent filars are not tightly packed involves the overall length of each filar. In particular, each filar will have a total length that is shorter than it would otherwise be if wound at a decreased pitch and with adjacent turns of a filar contacting one another. This decreased length of the filar in turn decreases the overall resistance of the filar, which is advantageous for many medical applications. Moreover, the decreased filar length further reduces the material costs needed to produce the filar. Additionally, if adjacent filars are not tightly packed such that adjacent filar turns do not contact one another when the coil is in a substantially "straight" configuration, certain coil configurations may have a larger bend radius at yield. This is because physical contact between the adjacent filars will not be a limiting factor in preventing a coil from flexing.

The data shown in FIG. 11A is provided for coils having filars that are solid MP35N and solid Ti-15Mo. However, similar results will be achieved for coils having filars with cores formed of a low-resistivity material. That is, if cores formed of a low-resistivity material of a same size are included in an MP35N coil as well as a Ti-15Mo coil, the relative comparison between such coils will remain the same as that shown in FIG. 11A. Specifically, the Ti-15Mo coil of an outer diameter of about 0.027 inches will still be capable of providing for three times the pitch as the MP35N coil of the same outer diameter. Moreover, the Ti-15Mo coil will still achieve a bend radius that is about 2.5 times smaller than the MP35N coil when both coils have an outer diameter of about 0.027 inches.

The data of FIG. 11A is specifically related to Ti-15Mo coils having a maximum pitch for the listed bend radius at yield. Similar results will be obtained for other beta titanium alloys. In other examples, beta titanium alloy coils having similar dimensions as those shown in FIG. 11A will exhibit up to a 0.1 inch maximum pitch while having a similar bend radius at yield. Thus, the superior results obtained for Ti-15Mo coils are likewise obtained for coils formed of other beta titanium alloys.

Figure 11B:
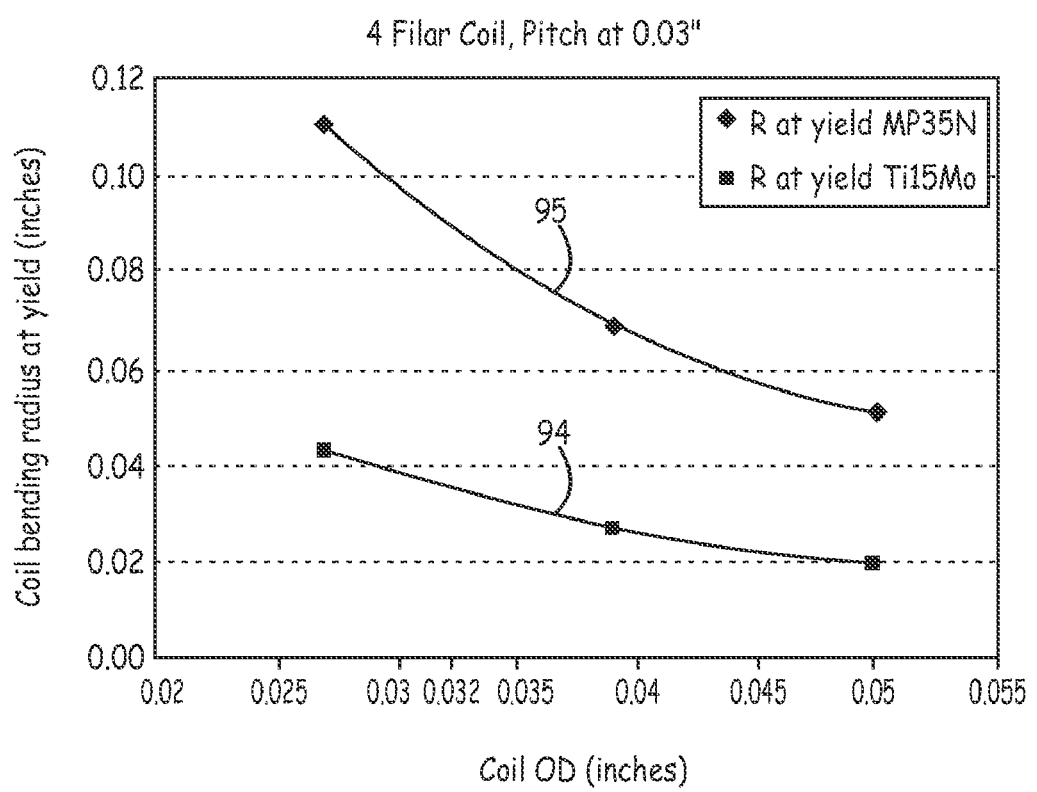
FIG. 11B is a graph comparing the bending radius at yield to coil outer diameter for a four-filar MP35N coil and a four-filar Ti-15Mo coil.

FIG. 11B is a graph comparing the bending radius at yield for a four-filar MP35N coil to that of a four-filar Ti-15Mo coil. The filars in this case have a diameter of 0.004 inches and the coils have a pitch of 0.03 inches. The bending radius at yield (in inches) is shown along the Y axis. The coil outer diameter (in inches) is depicted along the X axis. Curve 94 represents data obtained for the Ti-15Mo coil whereas curve 95 represents data obtained for the MP35N coil.

As shown by curve 95, the MP35N coil has a bend radius of about 2.5 times that of a corresponding Ti-15Mo coil having a same coil diameter. For instance, for a coil outer diameter of 0.027 inches, the Ti15Mo coil's bending radius at yield is about 0.043 inches whereas the coil bending radius at yield for a MP35N coil having the same outer diameter and pitch is about 0.11 inches (which is about 2.5 times that of the Ti15Mo coil). Similarly, at a coil outer diameter of 0.05 inches, the Ti15Mo coil's bending radius at yield is about 0.02 inches whereas the coil bending radius at yield for a MP35N coil having the same outer diameter and pitch is about 0.05 inches (again, about 2.5 times that of the Ti15Mo coil). This again shows the superior ability of the Ti-15Mo coil to bend without permanent deformation as compared to the MP35N coil. This is important in applications wherein the coil will be subjected to repeated strain with small bend radius.

Figure 11C:
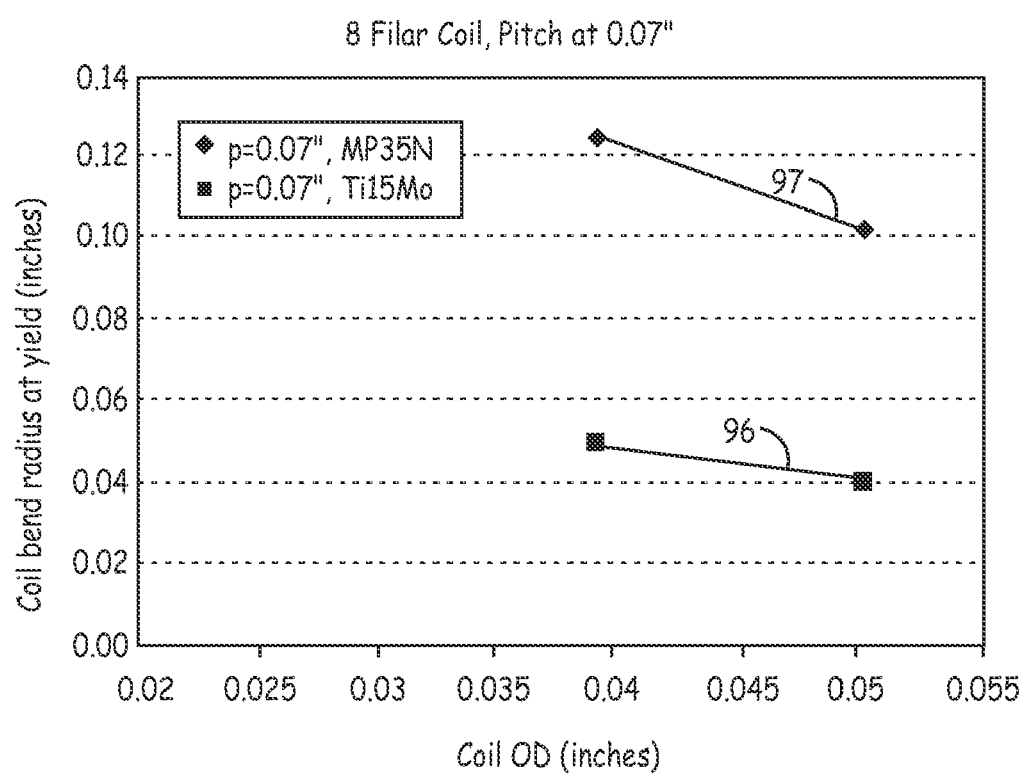
FIG. 11C is a graph comparing the bending radius at yield to coil outer diameter for an eight-filar MP35N coil and an eight-filar Ti-15Mo coil.

FIG. 11C is a graph comparing the bending radius at yield for an eight-filar MP35N coil to that of an eight-filar Ti15Mo coil. The filars in this case have an outer diameter of 0.004 inches and the coils have a pitch of 0.07 inches. The bending radius at yield (in inches) is shown along the Y axis. The coil outer diameter (in inches) is depicted along the X axis. Curve 96 represents data obtained for the Ti-15Mo coil whereas curve 97 represents data obtained for the MP35N coil.

As was the case with the four-filar coils represented by FIG. 11B, the MP35N coil has a bend radius of about 2.5 of a corresponding Ti-15Mo coil having a same coil diameter. For instance, for a coil outer diameter of about 0.039 inches, the Ti-15Mo coil's bending radius at yield is about 0.05 inches whereas the coil bending radius at yield for a MP35N coil having the same outer diameter and pitch is about 0.125 inches (which is about 2.5 times that of the Ti15Mo coil). Similarly, at a coil outer diameter of 0.05 inches, the Ti15Mo coil's bending radius at yield is about 0.04 inches whereas the coil bending radius at yield for a MP35N coil having the same outer diameter and pitch is about 0.10 inches (again, about 2.5 times that of the Ti-15Mo coil).

Figure 12:
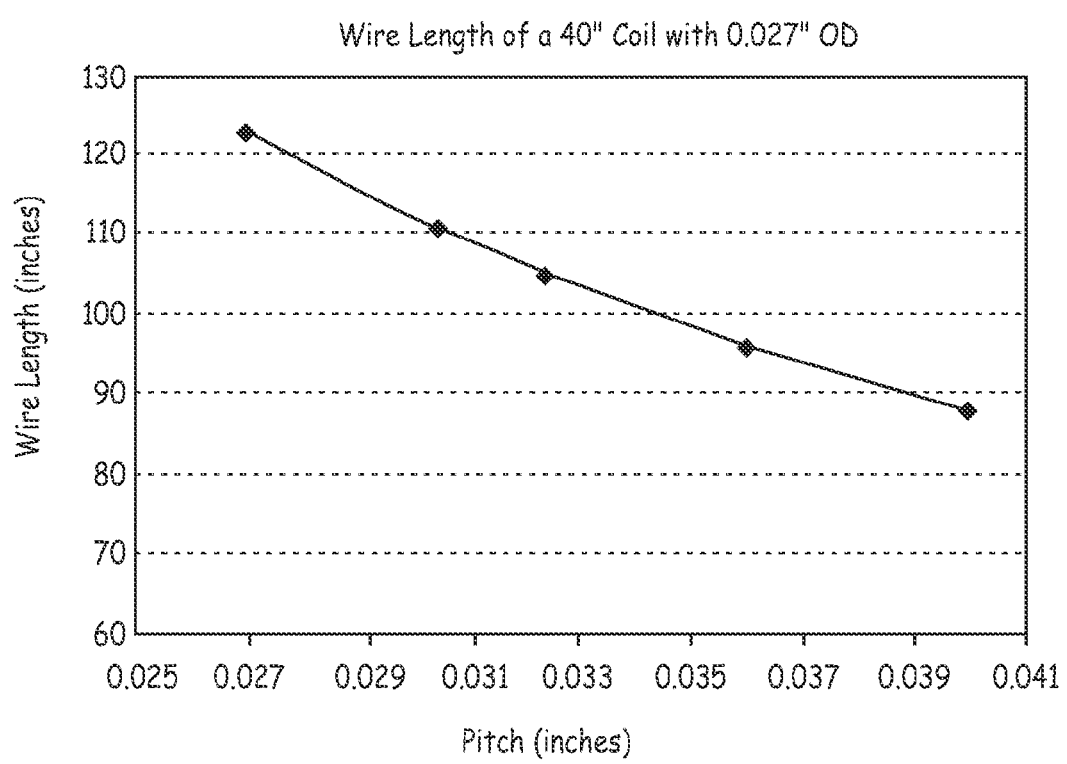
FIG. 12 is a graph comparing the coil pitch to the total length of wire required to form a coil.

Other advantages to using beta titanium alloys as compared to MP35N for coil applications are exemplified by FIG. 12.

FIG. 12 is a graph comparing the coil pitch to the total length of wire required to form a coil that is 40 inches in length having an outer diameter of 0.027 inches. As pitch increases (as shown along the x axis), the total length of material that is required to form the coil decreases (as indicated along the y axis). For instance, at a pitch of 0.027 inches, a little over 120 inches of wire is required to form the coil, whereas at a pitch of 0.039 inches, a little under 90 inches is required. Thus, over 25% less material is required for the coil having the larger pitch. This illustrates the advantage of using a material such as a beta titanium alloy that is capable of providing a wire having a very large pitch.

Besides decreasing material costs, the reduction in length achieved by increased pitch is important for another reason. The 25% reduction in overall length of a filar of a coil attained by increased pitch will directly translate into a 25% reduction in the resistance of the filar, helping to minimize power losses and overall device resistance.

Still another advantage of using Ti-15Mo coils relates to the elastic range provided by these coils, which is almost twice that of coils having MP35N filars. This is shown in FIG. 13.

Figure 13:
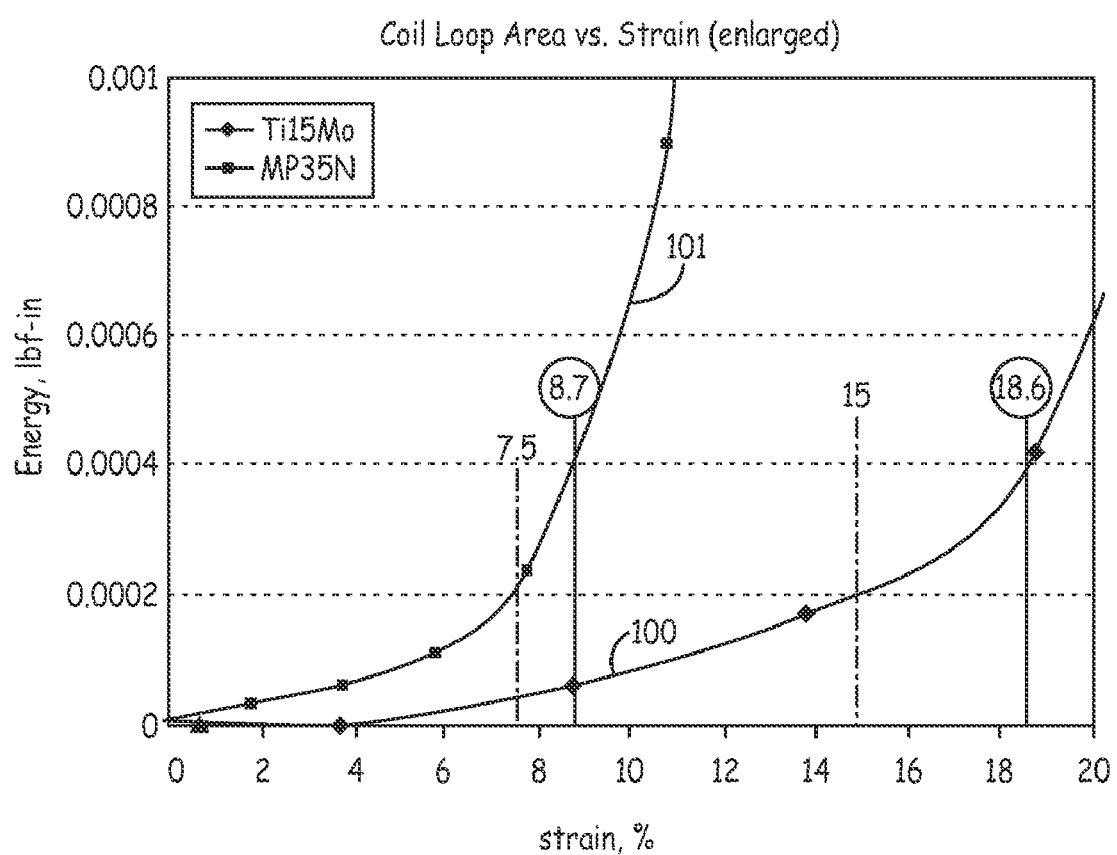
FIG. 13 is a graph illustrating an enlarged strain plot for Ti-15Mo and MP35N coils having the same outer diameter.

FIG. 13 is a graph illustrating an enlarged strain plot for a Ti-15Mo coil and an MP35N coil, wherein both coils have the same outer diameter. An amount of energy that is expended to exert strain on a coil is shown along the y axis in lbf-in. The amount of strain the coil undergoes (as a percentage) is represented along the x axis. Curve 100 illustrates that the Ti-15Mo coil has a much larger elastic range than that for the MP35N coil represented by curve 101. In particular, at an energy expenditure of 0.0002 lbf-in, the MP35N coil experiences a strain of 7.5%, versus a strain of about 15% for Ti-15Mo. Similarly, when 0.0004 lbf-in is expended, the MP35N coil undergoes a strain of about 8.7% versus a strain of 18.6% for the Ti-15Mo coil. This means that for a given amount of exerted energy, the Ti-15Mo wire has about twice the elongation as the MP35N wire. As a result, the Ti-15Mo coil allows for more "stretch", which is particularly important in applications wherein a medical device (e.g., a lead) carrying such a coil may be placed in an area of a body experiencing movement. A lead carrying a coil formed of one or more beta titanium alloy filars will stretch with the patient's movement to enhance patient comfort.

While in the foregoing discussion, the various characteristics of MP35N are compared specifically to the beta titanium alloy Ti-15Mo, this was for illustrative purposes only. A similar comparison may be made between MP35N and other beta titanium alloys with similar results. The beta titanium alloys provide important benefits over the MP35N for use in manufacturing coils for medical devices.

Whereas the foregoing describes the benefits of beta titanium alloys in the formation of coils, similar and other benefits are achieved when using the beta titanium alloys in cable arrangements.

As previously discussed, whereas a coil may be formed using a gathering or winding process that winds successive turns of the coil around a central axis, a cable may instead be formed by twisting together wires that were previously in a parallel configuration with respect to one another. Once so twisted, the cable may be heated to a stress-relieve temperature which will allow the twisted configuration to be retained once the "twisting" force has been removed.

Coils and cables exhibit very different properties. For instance, a coil will generally have a greater elasticity than a cable. As a result, when force is exerted on the coil, the coil will stretch to a relatively high percentage of its total length before permanently deforming or breaking A cable structure will not have the same degree of elasticity. Thus, a coil is able to withstand more longitudinal force than a corresponding cable structure having a same number of wires and being formed of the same material. On the other hand, the amount of material needed to form a coil is greater than that required to form a corresponding cable, and the coiling process may be more time-consuming, leading to higher manufacturing costs. Thus, the decision as to whether to utilize a cable or coil structure will be application-specific. In any event, using biocompatible beta titanium alloy wires of the type described herein (either with, or without, low-resistance cores) will provide important benefits both to coils and cables that are not available with MP35N wires.

Next, the discussion will turn to various examples of beta titanium alloy wires arranged in cable configurations.

Figure 14A:
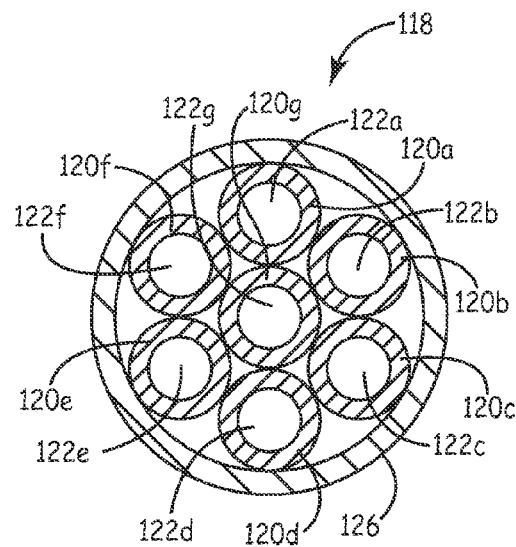
FIG. 14A is a cross-sectional view of one example of a cable according to the current disclosure.

FIG. 14A is a cross-sectional view of one example of a cable 118 according to the current disclosure. The cable 118 includes multiple wires. Each such wire may, in one example, be formed of a tube, or outer layer, of beta titanium alloy that directly surrounds a low-resistance core. In this embodiment, seven wires are shown, each including one of these tubes 120a-120g that may immediately surround a respective one of the cores 122a-122g. The seven wires may be twisted together in a manner to be described below in reference to FIG. 14B.

In the example of FIG. 14A, the wires of cable 118 are surrounded by a single insulating sheath 126, which may be a polymer that includes, but is not limited to, ethylene tetrafluoroethylene (ETFE), polytetrafluoroethylene (PTFE), silicone rubber or polyurethane. Other materials that act as electrical insulators may be used in the alternative. This sheath may be formed in an extruding process that wraps, or encases, the material around the cable. In another embodiment, a bare cable without sheath 126 may be located within a medical device (e.g., a lead) such that the body of the medical device may itself serve as the insulating sheath.

In another example, rather than be encased by sheath 126 that provides a substantially uniform layer around the wires of cable 118, the cable may instead be coated in a manner that "fills in the gaps" between adjacent wires. For instance, the cable may be fed through a slot or opening of a micro-extruder that applies a thin layer of a polymer such as ETFE to the entire surface of the cable so that the final cable has a predetermined diameter. The predetermined diameter may be selected so that the layer has at least some predetermined minimum thickness at its thinnest point. In one example, this predetermined thickness at its thinnest point is 0.001 inches. This is discussed further in regards to FIGS. 15A-15D.

In one example, all seven wires within cable 118 may be electrically coupled one to another. Each of these wires may then be electrically coupled to the same set of elements to provide redundancy. For instance, each of the wires of cable 118 may be electrically coupled to a same conducting electrode 38 and a same connector electrode 36 (FIG. 3A). In such a scenario, failures may occur in up to six of the wires of cable 118 without experiencing an open circuit, so long as one of the wires is still electrically coupling the two interconnected elements.

A particular embodiment of the foregoing may include seven un-insulated wires, each having a diameter of between 0.00133 inches-0.00167 inches. The bare 1×7 cable (excluding insulating sheath 126) of such an example may have a diameter of between 0.004 inches-0.005 inches.

In another embodiment, one or more of the wires of cable 118 may be provided with a respective insulating sheath so that these one or more wires are not electrically coupled to at least some of the other wires included in the cable. This may allow some wires to be electrically coupled to a respective set of elements (e.g., a conducting/connector electrode pair) while other ones of the wires within the same bundle are electrically coupled to a different respective set of elements. In a specific example, all of the wires may be provided with respective insulating sheaths so that each of the seven wires in cable 118 is capable of transmitting a different respective signal. Thus, the wires of cable 118 may be configured in many different ways.

It will be appreciated that any desired degree of redundancy may be provided by a cable of the type shown in FIG. 14A, with the number of wires that may be included within the cable being limited by the outer diameter of the wire and the desired outer diameter of the cable. In some examples, at least one of the wires, such as the central wire, may have a different diameter than the other wires. For instance, a central wire may have a larger diameter than other surrounding wires. Thus, many cable arrangements are possible within the scope of this disclosure.

Figure 14B:
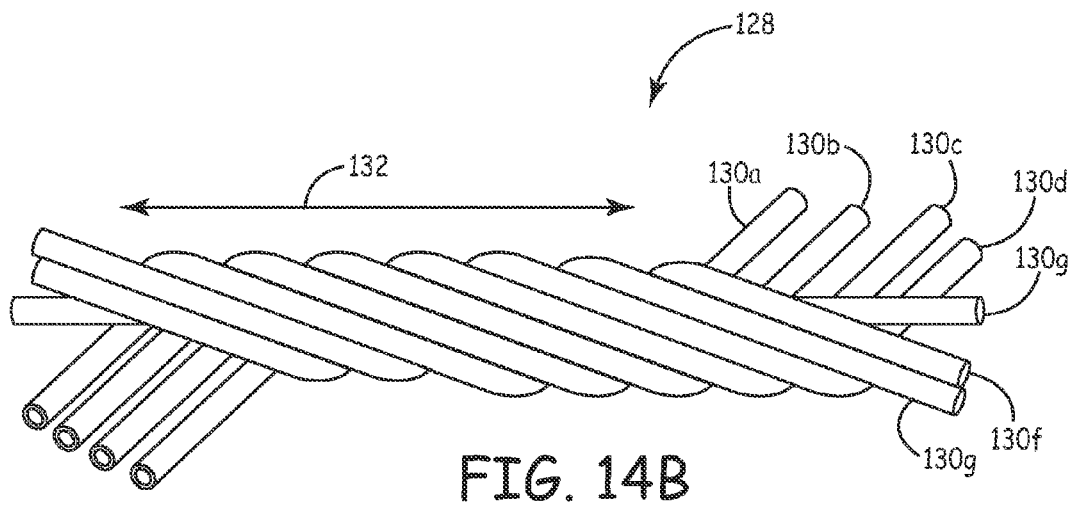
FIG. 14B is a side view of a cable according to one embodiment of the disclosure.

FIG. 14B is a side view of a cable according to one embodiment of the disclosure. This view shows a cable 128, which may be of a type such as shown in FIG. 14A. This cable comprises wires 130a-130g, each of which may have a low-resistance core and an outer surrounding layer formed of beta titanium alloy. As previously discussed, to construct this cable, the wires may be arranged in a substantially parallel configuration with the ends being held under a predetermined amount of force. A twisting action is exerted on one or both ends to twist the wires together.

In one example, during manufacturing, each of the multiple wires is retained on a respective spool. An end of each such wire is unwound from the spool and threaded into a respective retaining member that retains that wire in a predetermined relationship with respect to the other wires. For instance, to form a cable of the type shown in FIG. 14A, the retention members would retain an end of one wire in a central location with six additional retention members retaining six additional wires around the central wire. While the retention members are maintained in this fixed relationship to one another, at least some of the retention members may be rotated as the wires are unwound from the spool to form the cable. Of course, other mechanisms are available to twist the wires, and this is merely one example.

After being twisted together in this manner, and while the ends of the wires are retained under stress (e.g., to retain the wires in the twisted configuration), the entire length of the cable may be heated to a stress-relieve temperature that allows the wires to remain in this twisted configuration after the twisting force is removed. This heating may be done by passing the length of the cable through a heated chamber while the wires of the cable are still under stress so that each point in the cable is heated to the stress relieve-temperature. Heating the cable to the stress-relieve temperature changes the physical properties of the wires and the cable as a whole, allowing those wires to remain twisted in a rope-like configuration even after the twisting force has been removed.

As previous discussed, each of the wires in FIGS. 14A and 14B may be of a type described herein having a beta titanium alloy outer layer surrounding a low-resistance core. One benefit of using this type of wire in the cabling process as opposed to MP35N involves the superior characteristics of the wire following heating to the stress-relieve temperature. The stress-relieve temperature that is required to form a cable of multiple MP35N wires ranges from 500° C.-850° C. Heating the MP35N to such temperatures causes the MP35N wires to become brittle and inflexible. As a result, when subjected to repeated stress (e.g., bending), the wires may weaken and require replacement. This shortens the life of the medical device (e.g., lead) that carries the cable formed of the MP35N wire(s).

In contrast to MP35N wires, beta titanium alloy wires do not become brittle at their stress-relieve temperature. As one example, stress-relieve heating can be performed at temperatures of between 500° C.-850° C. for under 20 seconds for any of the biocompatible beta titanium alloys. In a particular example, a cable formed of Ti-15Mo wires may be heated to a stress-relieve temperature of between 500° C.-650° C. for under 20 seconds without becoming brittle. One even more specific scenario uses a temperature of between 600° C.-650° C. which is maintained for under 10 seconds for a Ti-15Mo cable. Heating to a temperature of 625° C. for 9 seconds may be used for this purpose in yet another embodiment.

In any of the foregoing cases, the physical characteristics of the wires, as well as the cable comprising the wires, will be changed based on heating to these temperatures for these time periods. For instance, after heating to the foregoing temperatures, the Ti-15No wires carried by the cable are ductile, and can undergo a high amount of strain. A similar result is obtained for any of the other beta titanium alloys discussed herein: the wires and resulting cable structures will not become embrittled at their respective stress relieve temperatures, which will range from between about 500° C.-850° C.

Other benefits similar to those set forth above with respect to coils are obtained when using beta titanium wires to form cable structures. Beta titanium alloy cables are more biocompatible and do not present corrosion issues resulting from metal ion oxidation. Moreover, a cable formed of beta titanium wires will have a much higher fatigue endurance limit and better kink resistance than a cable that comprises MP35N wires. As a result, the cables have a longer life. Additionally, such cables will have a decreased bend radius because of the lower elastic modulus of the beta titanium alloy as compared to that of MP35N. This results in medical electrical devices (e.g., leads, etc.) that can be more easily steered into a desired location within the body and which are more comfortable for the patient. Use of the beta titanium alloy wires further allows the cables to be more weld-compatible with other materials commonly used in medical devices, including Pt, Pt alloys, Ta, Ta alloys, Nb and Nb alloys.

As another benefit, in a cable embodiment wherein one or more of the beta titanium alloy wires includes a respective low-resistance core, it is possible to tune the resistance of each such wire. This may be accomplished by selecting the fraction of the core cross-sectional area to that of the overall wire cross-sectional area, as is discussed above with respect to FIG. 7. The cable resistance may be approximated as the in-parallel resistance of the individual wires in one embodiment. That is, the cable resistance may be modeled as multiple parallel resistors, with each resistors having a resistance of a respective one of the wires. As such, after tuning the resistances of the individual wires, the cable resistance can be further tuned by selecting the number of wires to include in the cable. In this manner, the resistance of the cable can be tuned to be similar to, or the same as, a component to which the cable will be electrically coupled. For instance, the cable can be tuned to have the same, or a similar resistance, as an electrode to which it will be coupled, thereby minimizing signal reflections. This can decrease the amount of power needed to send and receive signals. Such tuning is not feasible with silver-cored MP35N wires for reasons previously described.

Still other benefits can be obtained by using beta titanium alloys to provide cable structures that are better suited for MRI conditionally-safe use than silver-cored MP35N. For instance, a higher resistance wire can be provided by selecting such alloys as Ti-15Mo, TLC, and TNCZ instead of MP35N, since these alloys have a higher resistivity than MP35N. In an application wherein the wires comprise an inner core such as shown in FIGS. 14A and 14B, niobium or tantalum may be selected for use as the core material, since either material exhibits a significantly higher resistivity than silver. The resulting cable will have a higher resistance than a cable formed of silver-cored MP35N wire, thereby reducing heating for MRI applications.

Yet another benefit of using beta titanium alloy cables results from the fact that the beta titanium alloy wires 130a-130g may be fully annealed without melting the inner low-resistance cores. The wires are therefore ductile, further improving the fatigue life of the cable.

Returning again to the cable of FIG. 14B, it may be noted that the cable may have a "lay" that is similar to the pitch described above with respect to a coil. This lay is the distance between adjacent twists of the same wire, as shown by arrow 132. In one example, the lay will be between 0.019 inches to 0.06 inches. In a more specific example involving a 1×7 cable, the lay may be in the range of between 0.038 inches to 0.06 inches. For a 1×3 cable, the lay may be in the range of between about 0.019 inches and 0.04 inches. Thus, the lay may be at least partially dependent on the number of wires included in the cable.

As may be noted, in the examples of FIGS. 14A and 14B, there is a center wire (e.g., wires 122g and 130g, respectively) within the cable that may not be twisted with the rest of the wires, but instead runs along the center of the coil. This wire runs substantially along a longitudinal axis of the cable. Because this central wire is not in a twisted configuration, it will not be able to sustain a same level of strain as the other wires. In other words, this central wire may have more susceptibility to bending and longitudinal stress than the other wires in the cable. Therefore, it may be advantageous in some examples to eliminate this center wire in favor of a cable configuration in which every wire has a twisted configuration. This is discussed further below.

FIGS. 14A and 14B further illustrate a difference between a cable and a coil discussed above. A cable is a solid structure having no central longitudinal axis that defines an inner space, or "air core", running the length of the cable. Thus, with a cable design, there is no space in which to insert a steering device as is the case in some coil designs discussed above. This is discussed below in regards to lead designs using cable structures.

In the above descriptions of both coils and cables, example wires have been described primarily as having low-resistance cores surrounded by a layer of a biocompatible beta titanium alloy, which may be described as a "tube" of this material. In other examples, it may be desirable to utilize biocompatible beta titanium alloy wires that are formed completely of that alloy and which omit the low-resistance core. In fact, in embodiments wherein low resistance and/or tuning are less important considerations, there may be no need to include a low-resistance core. A wire without a core may be less expensive to manufacture, resulting in lower device costs.

In accordance with the foregoing, it should be understood that any of the coil or cable structures described herein may be formed of wires made completely from the biocompatible beta titanium alloys described herein but that omit the low-resistance cores. That is, the wires are solid beta titanium alloy structures to their center, with the core being "replaced" instead by beta titanium alloy material. These coil and cable structures will exhibit many of the properties discussed above, having characteristics that are superior to coil or cable structures formed of MP35N wires. In particular, the benefits listed in Table 3 (excluding tunability and minimizing resistance) may be achieved by beta titanium alloy wires regardless of whether low-resistance cores are provided.

Further in regards to coil configurations, the properties of coils set forth in Table 4 above are achieved by beta titanium alloy wires regardless of whether those wires have low-resistance cores or are made completely of beta titanium alloy. Such properties include the ability to achieve increased pitch (and hence increased filar count) for a given outer coil diameter as well as the ability to achieve a smaller coil outer diameter for a coil having the same number of filars. As another example, the benefits achieved by the coil configurations of FIG. 10A-10C could largely be obtained from coils formed of wires with, or without, the low-resistance, cores (exclusive of tunability and minimizing resistance).

In regards to cable structures, the embrittlement issues related to heating of an MP35N cable to a stress-relieve temperature during a cabling process are eliminated by using beta titanium alloy wires regardless of whether those wires include low-resistance cores.

Because the low-resistance cores are not needed to achieve many of the benefits described herein, it should be understood that any of the coil or cable embodiments described and/or shown herein may comprise wires formed completely of biocompatible beta titanium alloy wires that exclude the low-resistance cores. As such, several specific cable examples that omit low-resistance cores are next considered for illustration purposes.

Figure 15A:
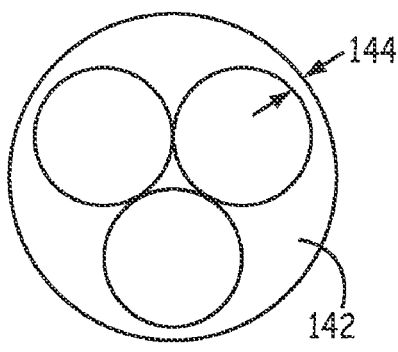
FIG. 15A is a cross-sectional view of a cable formed of wires that do not have low-resistance cores.

FIGS. 15A-15D are cross-sectional views of various cable examples formed of biocompatible beta titanium alloy wires in the manner discussed above. These wires may be cabled together in a manner similar to that described above with respect to FIGS. 14A and 14B. In FIG. 15A, three wires are contained within the cable. For the cable of FIG. 15B, four or five wire may be included in the cable, with an optional fifth wire 141 (shown dashed) running down the center of cable. This optional fifth wire 141 has a diameter that is smaller than that of the other four wires. The cable of FIG. 15C includes four wires in an oblong configuration, with one pair of oppositely-situated wires 143a, 143b being in contact with each other, whereas the other pair of oppositely-situated wires 145a, 145b are not in contact with each other. This may provide a more stable configuration than a four-wire configuration of the type shown in FIG. 15B (that is, when optional central wire 141 is omitted).

Figure 15B:
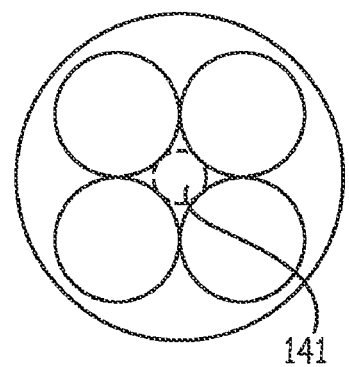
FIG. 15B is a side view of a coil formed of independently-insulated filars that do not include low-resistance cores.
Figure 15C:
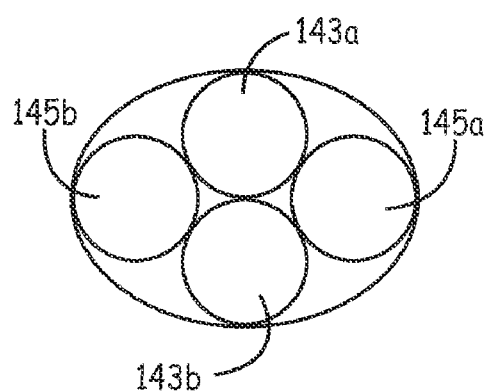
FIGS. 15C-15D are cross-sectional views of various cable examples formed of wires that do not have low-resistance cores.

Except for the configuration of FIG. 15B that includes optional center wire 141, the configurations represented by FIGS. 15A-15C do not include a central wire. In such configurations, when cabling is performed in a manner similar to that shown in FIG. 14B, all of the wires in the cable will be twisted at a similar lay. This may result in a cable having better strain tolerance.

The bare cables (i.e., the cables excluding the insulating layers) of FIGS. 15A-15C may have diameters of between 003 inches-0.010 inches in one embodiment. In a more specific example, the cables may have an outer diameter of between 0.004 inches-0.005 inches. When insulating sheaths are applied, the cables of the latter example may have an outer diameter of about 0.005 inches-0.006 inches.

In one example, the three to four larger wires forming the cables of FIGS. 15A-15C may have diameters of between 0.0010 inches-0025 inches. In a more specific example, the diameters of these wires may be between 0.0018 inches-0.0024 inches with the smaller central wire 141 of FIG. 15B having a diameter of between about 0.006 inches-0.008 inches. Many other examples are possible.

Figure 15D:
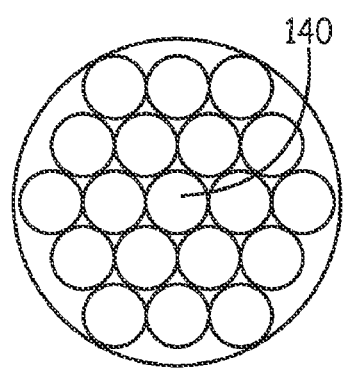

FIG. 15D is a cross-section view of yet another type of cable according to techniques described herein that includes a central wire 140. Six intermediate wires are directly adjacent to this central wire 140. Twelve additional wires surround the intermediate wires. As was described above with respect to FIGS. 14A and 14B, the central wire 140 will not be twisted along with the other wires but instead will run substantially down the middle of the cable. Since this central wire is not twisted (and thus has no enhanced capability to "give" or stretch when stress is exerted on the cable), the central wire may experience a higher level of strain than the other wires. For this reason, it may be desirable to utilize a configuration wherein all wires are twisted, as shown in some examples of FIGS. 15A-15C.

Figure 15E:
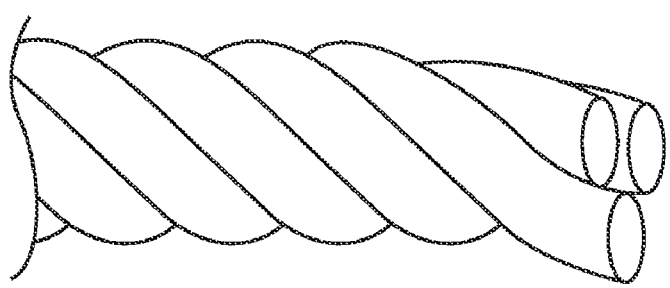
FIG. 15E is a side perspective view of a cable such as shown in the cross-sectional view in FIG. 15A.

FIG. 15E is a side perspective view of a cable such as shown in cross-sectional view in FIG. 15A. This view again shows that there is no central wire running the length of the cable, and thus all wires in the cable may be capable of sustaining a same amount of strain.

As is the case described above with respect to FIG. 14B, the cables of FIGS. 15A-15E have a lay. For a cable such as shown in FIGS. 15A and 15E having three wires, the lay may be between about 0.019 inches and 0.04 inches in one example. Other embodiments are possible, however.

In all cases, the cables of FIGS. 15A-15E may be formed according to methods discussed above with respect to FIGS. 14A and 14B. In particular, once the wires are twisted together, the twisted cable may be heated to a stress-relieve temperature. As previous discussed, one benefit of using the beta titanium wire in the cabling process as opposed to MP35N wire involves the superior characteristics of the wire following heating to the stress-relieve temperature for cabling. In contrast to MP35N wires, beta titanium alloy wires, including Ti-15Mo wires, do not become brittle at the stress-relieve temperature. As one example, the stress-relieve heating for cables formed of beta titanium alloys, including examples shown in FIG. 15A-15E, can be performed at a temperature between about 500° C.-850° C. In a more specific example, such heating may occur between about 500°

C.-650° C. for less than 20 seconds for Ti-15Mo wires. An even more specific scenario uses a temperature of 625° C. which is maintained for less than 10 seconds (or approximately 9 seconds in one particular example) to ensure that a Ti-15Mo cable is set in a twisted configuration. Thereafter, the beta titanium alloy wires carried by the cable (and indeed, the cable itself) are ductile, and can undergo a high amount of strain. Thus, in all such examples, heating to these temperature ranges for these times changes the physical attribute of the cables, allowing the cables to retain its shape even after the twisting force is removed.

Returning to the cross-section views of FIG. 15A-15D, the illustrated cables are shown to have a solid coating surrounding the wires that defines a generally circular or oblong profile for these examples. For instance, unlike coil 118 of FIG. 14A which carries a sleeve 126 having a substantially uniform thickness that surrounds the seven wires while allowing some "open space" to remain between adjacent wires, the cable of FIG. 15A has a solid coating 142. Such a coating may be formed using a micro-extrusion process that encases the cable within the insulating material 142. To accomplish this, the length of the cable may be fed through a micro-extruder that applies a thin layer of a biocompatible polymer such as ETFE to the entire surface of the cable so that the final cable has a predetermined shape and size. The layer may be applied so that at a thinnest point, at least some predetermined minimum thickness is provided, as indicated by arrows 144 of FIG. 15A. In one example, this predetermined thickness is 0.001 inches. In other examples, any of the embodiments of FIGS. 15A-15E could include an insulating sheath or sleeve having a uniform thickness, as illustrated in regards to FIG. 14A rather than carrying a solid layer of insulating material.

In the cable examples of FIGS. 15A-15C having between three and five wires, the wires may be of a larger diameter than cables of a similar diameter that include more wires, such as shown in the 1×19 cable example of FIG. 15D. This may be desirable to decrease resistance of the wire in low-frequency applications. However, in higher-frequency applications, it may be desirable to include more wires per cable (even if such wires have a smaller diameter). This is because when higher frequencies are used, a "skin effect" may be exhibited, with current traveling primarily along the surface of the wire. In such cases a higher-strand cable having smaller wires will exhibit a lower resistance than a cable with fewer larger wires.

As previously discussed, in cable configurations, all of the wires in the cable may be electrically coupled one to another. In other embodiments, one or more of the wires may be provided with a respective insulating layer to insulating the wire electrically from the other wires in the cable. This may allow the wires that are so insulated to carry a different signal that than is being carried substantially simultaneously by other ones of the wires in the cable.

Figure 16A:
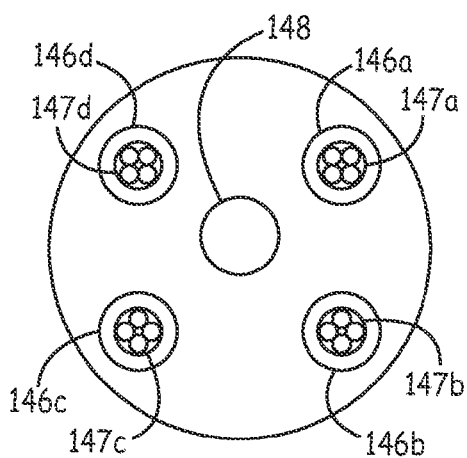
FIG. 16A is a cross-sectional view of a medical electrical lead that may carry multiple cables.
Figure 16B:
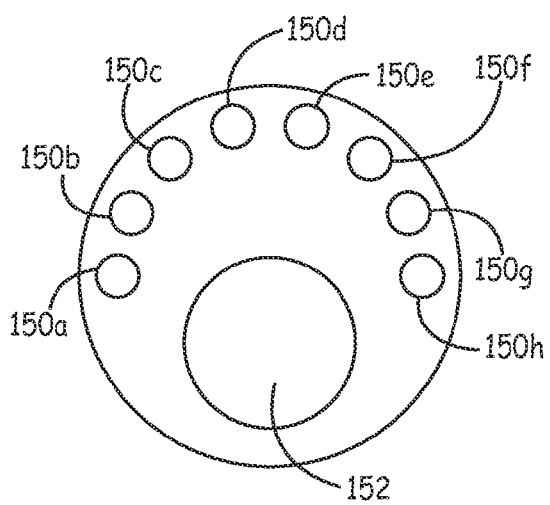
FIG. 16B is a cross-sectional view of another example medical electrical lead that may carry multiple cables.
Figure 16C:
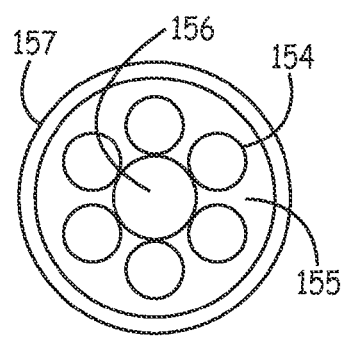
FIG. 16C is an example of a medical electrical lead that carries a single cable.

One or more cables of the type described herein may be carried by an implantable medical device, as discussed in regards to FIGS. 16A-16C.

It may be noted again that all cable configurations of FIGS. 15A-15E, and indeed all cable configurations described herein, could include low-resistance cores, if desired. Similarly, all coil configurations described herein may, but need not, include the low-resistance cores.

FIG. 16A is a cross-sectional view of a medical electrical lead of one embodiment. The lead includes four peripheral lumens 146a-146d, each of which carry a respective cable 147a-147d, each of which may be any of the types described herein or variants thereof. In the particular example, the cable includes four wires and is configured in a manner similar to that shown in FIG. 15B. Each such cable may extend between, and electrically couple, a respective pair of conducting/connector electrodes of the type shown in FIG. 3A. In such an example, each conducting electrode may be used to deliver an electrical signal independently of the other conducting electrodes. For instance, all four conducting electrodes 38 (FIG. 3A) could deliver independent signals substantially simultaneously to tissue in an example wherein IMD 12 has four independent stimulation channels. Alternatively, some or all of the conducting electrodes 38 could be used to sense signals (e.g., while other electrodes provide stimulation, for instance.)

The embodiment of FIG. 16A further provides a central lumen 148 which may receive a guiding device such as a stylet or guide wire used to place the lead during implantation. In another embodiment, lumen 148 could receive a sensing device or another device, such as a fiber for delivering optical stimulation to tissue, a sensor to sense a signal from the tissue, or a device to deliver a pharmacological agent. In another embodiment, lumen 148 may be omitted.

Each of the cables shown in FIG. 16A are illustrated as including an insulating layer that surrounds the four wires of the cable. In such an embodiment, the insulating layer is stripped away from the cable at the location wherein the cable is to be electrically and mechanically coupled to a respective electrode, such as a conducting electrode 38 or a connector electrode 36 (FIG. 3A). The stripped portion of the cable may then be mechanically and electrically coupled to the respective electrode by, for instance, a crimping mechanism and/or a spot weld, laser weld, or soldering process.

In another embodiment, one or more of the cables 147a-147d need not include an insulating layer since the body of the lead provides the insulation. In this case, stripping of the layer to perform the electrical coupling to the connector or conducting electrodes need not be performed.

In yet other embodiments, one or more of cables 147a-147d may couple together other structures besides connector/conducting electrode pairs. For instance, the lead may carry one or more sensors at the lead distal end which may be coupled via one or more of cables 147a-147d to another structure (e.g., a connector electrode) at the lead proximal end. Any other structure that needs to be electrically coupled to a corresponding structure at the lead proximal end may be so coupled through one or more of the cables.

FIG. 16B is another cross-sectional view of a medical electrical lead that may carry multiple cables. In this case, eight lumens 150a-150h are shown, each for receiving a respective cable which may be any of the cables described herein or variants thereof. Thus, in this instance, a lead carrying eight conducting electrode pairs could each be electrically coupled to a respective one of the cables so that eight signals could be transferred (e.g., sensed or delivered to tissue) substantially simultaneously by the electrodes. As was the case with the example of FIG. 16A, a lumen 152 is provided to receive a device, which may provide navigating/steering capabilities or may be another type of device for sensing, delivering stimulation (electrical or optical), delivering a pharmacological agent, or performing some other task. In another embodiment, lumen 152 may be omitted. In such an example wherein the lumen 152 is omitted, the lead could be placed at a location in a body using a steerable sheath rather than a guiding device positioned within the lumen.

FIG. 16C is yet another example of a medical electrical lead that includes only a single cable 154 within a central lumen 155. In this case, the cable is shown to exclude an insulating layer, with the lead body 157 itself providing the insulation. This type of configuration may be desirable if a lead having a very small diameter is required.

This example further shows that the central wire 156 of the cable may be larger than the other wires 154, if desired. This cable may be used to electrically and mechanically couple a single conductor/connector electrode pair. In another example, it may be possible to provide insulating layers for one or more of the individual wires within the cable so that the wires so insulated could electrically couple a different pair of structures (e.g., connector/conducting electrode pairs) than others of the wires. Thus, many configurations are possible.

Figure 17:
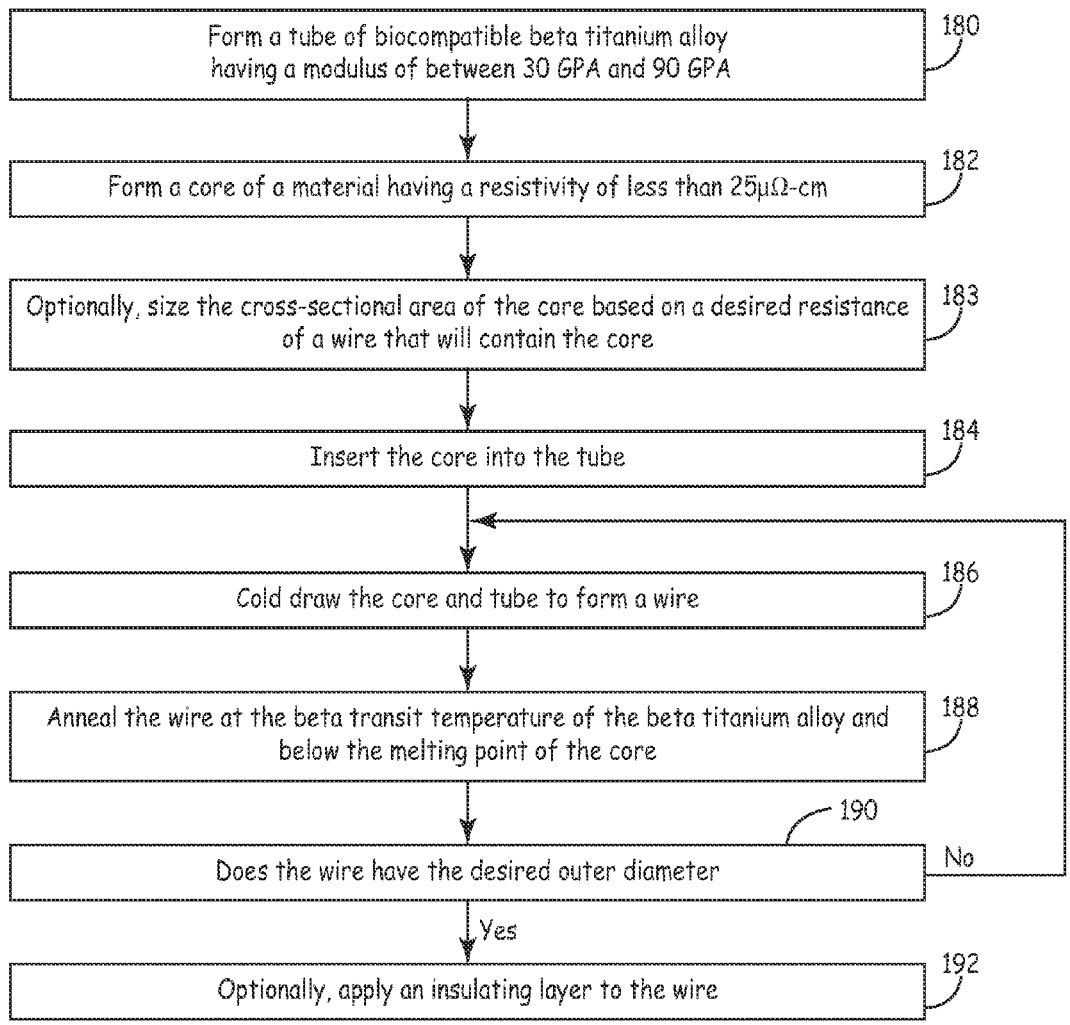
FIG. 17 is a flow diagram of one method of forming a wire according to one example of the disclosure.

FIG. 17 is a flow diagram of one method of forming a wire according to one example of the disclosure. First, a tube is formed of a biocompatible beta titanium alloy (180). The tube may have an inner diameter of between 0.1 inches to 2 inches (or between about 0.25 cm-5.0 cm). The beta titanium alloy from which the tube is formed exhibits the body center cubic (BCC) structure of titanium and may have a modulus of between 30 GPa and 90 GPa.

Next, a core may be formed of material possessing a resistivity of less than 25 micro-ohm-cm (182). Silver, which has a resistivity of 1 micro-ohm-cm may be used for this purpose. In a different example, the material used for this purpose possesses a resistivity of between 10 micro-ohm-cm and 20 micro-ohm-cm, and may be a material such as tantalum, niobium, or any other biocompatible materials discussed herein or known in the art that have such a resistivity. This core may be formed by cold-working the core material, or by heating and drawing it. The diameter of the final core is use-dependent and is sized to readily be inserted within the inner lumen of the beta titanium alloy tube.

In one example, the diameter of the core may optionally be sized so that after a wire has been drawn from the tube and core, the wire will have a desired predetermined resistance (183). In particular, the core diameter may be selected so that in the finished wire, the core cross-sectional area is a predetermined percentage of the cross-sectional area of the wire as described above with respect to FIG. 7. In this manner, the resistance of the end-product wire is selectable, and may be tuned for a particular application. For instance, the core may be formed to have a relatively large cross-sectional area if a relativity low resistance wire is desired. Alternatively, a relatively small cross-sectional area may be selected for the core if the resulting wire is to have a higher resistance. The selected resistance of the wire may be tuned to that of an interconnecting structure such as a conducting or connector electrode.

The core may be inserted into the tube (184), and the core and tube may be cold drawn (as in drawing it through a die of a predetermined size) to form a wire. (186). This wire may be annealed at the beta transit temperature of the beta titanium alloy and below the melting point of the core to obtain a ductile wire (188). This annealing step will change the physical properties of the wire, allowing the wire to retain ductility so that it may optionally be submitted to another cold drawing step. Because the beta titanium alloy will not become brittle at the annealing temperature, such a wire will not have the embrittlement issues associated with silver-core MP35N wires.

If a wire having a desired outer diameter has been obtained (190), processing may continue to step 192 where a layer of insulating material may optionally be applied to the wire. In one example, this involves dipping the wire in a liquefied ETFE to coat the wire, and then allowing the insulation material to solidify. Any other biocompatible insulating material may be used instead as discussed herein, and other processes such as extrusion may be used to apply this material.

If the desired outer diameter has not been obtained in step 190, processing may return to step 186 wherein the wire is re-drawn through another die having yet a smaller diameter and the wire is re-heated as shown in step 188. Steps 186 and 188 may be repeated any number of times to obtain a wire having a desired diameter.

In one example, the final wire may have a low-resistance core that is, in one embodiment, surrounded by an unbroken layer of the beta titanium alloy, with the wire having a diameter of between 0.001 inches-0.01 inches. Other diameters may be used in other examples.

Figure 18:
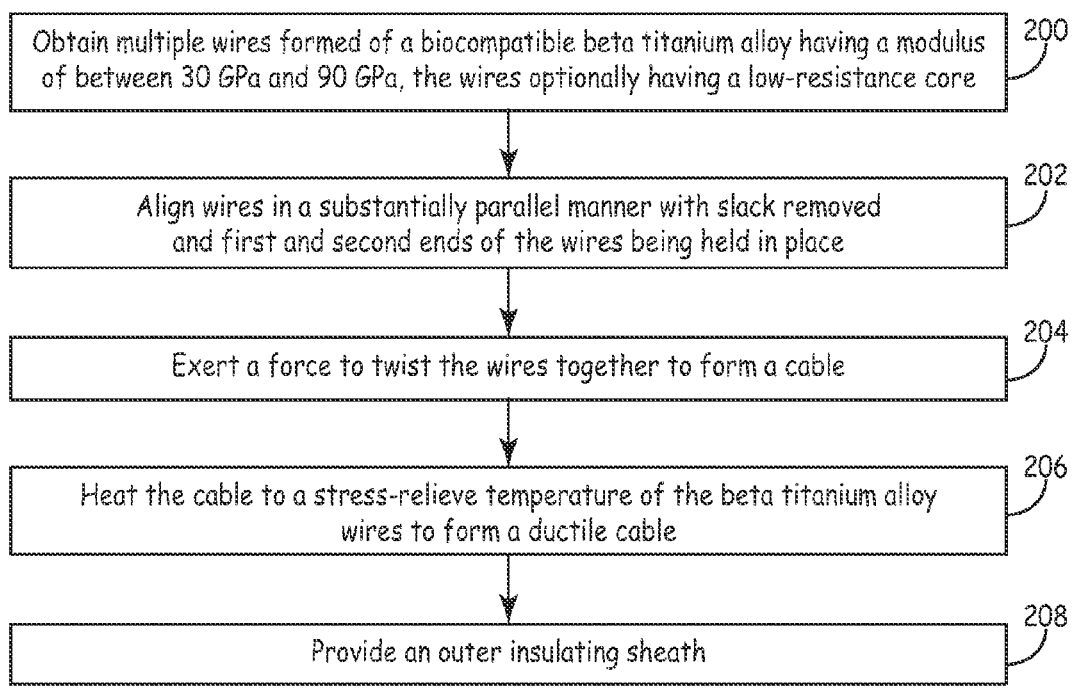
FIG. 18 is a flow diagram of a process according to one specific cable embodiment of the current disclosure.

FIG. 18 is an example flow diagram of a manufacturing process according to one specific cable embodiment of the current disclosure. Multiple wires formed of a biocompatible beta titanium alloy wires having a modulus of between 30 GPa and 90 GPa may be obtained, each optionally having a low-resistance core (200). While generally wires used to form a same coil will either all have cores or none will have cores, this need not be the case. In another example, only some wires need have cores. This may be desirable, for instance, if a lead carries different types of electrodes, and various filars of a coil are being tuned for connection to different ones of the electrodes. Optionally, one or more of the wires may be provided with a respective insulating layer.

Next, the wires may be aligned in a substantially parallel manner with slack removed and ends of the wires being held securely in place (202). A force may be exerted at first ends of the wires, or opposing forces may be exerted on both ends of the wires to twist the wires together to form a cable (204). As discussed above, this may be accomplished by threading ends of wires into retaining members and twisting one or more of the retaining members as wires are uncoiled from spools, thereby forming the twisted cable. The cable may then be heated to a stress-relieve temperature of the beta titanium alloy wires to form a ductile cable (206). A particular embodiment heats the cable to between about 500° C.-650° C. for less than 20 seconds for Ti-15Mo wires. One specific scenario uses a temperature of 625° C., which is maintained for less than 10 seconds. This heating will change the physical properties of the cable, allowing the cable to remain twisted even after the twisting force is removed.

An outer insulating sheath may be provided (208). For instance, the cable may be dipped in liquefied ETFE. Any other biocompatible insulating material may be used for this purpose. Alternatively, an extrusion process may be used to apply the insulating sheath to the cable.

Figure 19:
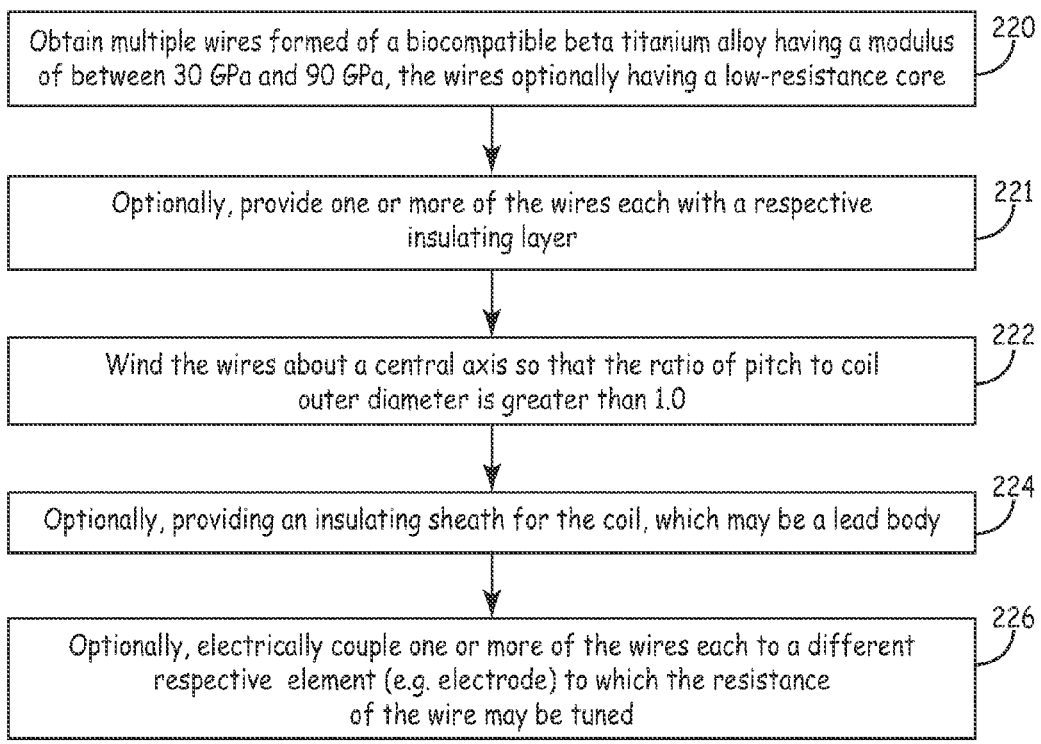
FIG. 19 is a flow diagram of another process according to one specific coil embodiment of the current disclosure.

FIG. 19 is a flow diagram of another manufacturing process according to one specific coil embodiment of the current disclosure. Multiple wires formed of a biocompatible beta titanium alloy wires having a modulus of between 30 GPa and 90 GPa may be obtained, each optionally having a low-resistance core (220). For instance, twelve such wires may be obtained. Optionally, one or more of these wires may be provided with a respective insulating layer (221). The wires may be wound about a central axis to form a multi-filar coil, with the ratio of the coil pitch to the outer coil diameter being greater than one (222). In specific examples, this ratio may be two or three.

In one instance, the wires are wound around a mandrel to form the coil, with the mandrel being removed after winding is completed. In a specific example, at least some of the multiple filars may be electrically insulated one from another or all of the filars may be insulated in this manner. This may be achieved by providing each of the wires used to form the coil with a respective insulating coating, such as a coating of ETFE.

Optionally, an insulating sheath may be provided for the coil (224). In one embodiment, the insulating sheath may be a lead body that carries the coil. One or more of the filars of the coil may each be electrically and mechanically coupled to a different respective element, such as a conducting electrode and/or a connector electrode (226). In a specific embodiment, each of the filars may be coupled to a different conducting/connector electrode pair to transmit a respective electrical signal therebetween. Thus, in the specific scenario wherein the coil includes twelve filars, up to twelve conducting/connector electrode pairs may be so connected to independently transmit twelve signals simultaneously via the filars of the coil. In some examples, one or more filars carrying cores may optionally have resistances that are tuned to approximate or match the resistances of element(s) to which the filar(s) are coupled.

In another example, the inner lumen of the coil defines a space that may receive a guiding device such as a stylet, guide wire, or some other guiding mechanism that can be used to position the coil (and the device that carries the coil) within a living body.

Various concepts are described herein. Each concept may be used alone or in conjunction with some, or all, of the other concepts described herein. As examples, any of the biocompatible beta titanium alloys described herein may be employed to form wires used to construct any of the coil configurations or variants thereof described herein. Moreover, one or more such wires may, but need not, include cores. Wires that do include cores may, but need not, have resistances that are tuned for a given application. Similarly, any of the biocompatible beta titanium alloys described herein may be employed to form wires used to construct any of the cable configurations or variants thereof described herein. Moreover, one or more such wires may, but need not, include cores, and the wires may optionally have resistances that are tuned.

In some instances, one or more coils and/or one or more cables of any of the types described herein may be carried by a same medical device. For instance, in a device such as represented by FIG. 16B, a coil of the type described herein may be carried by central lumen 152, with cables of any of the types described herein being carried by the peripheral lumens 150a-150h. Thus, many combinations and adaptations are possible.

It may further be appreciated that in the methods described herein, some of the steps may be re-ordered within the scope of the disclosure. Moreover, some steps may be omitted entirely. For instance, in some cases, an insulating sheath or layer need not be provided for a wire, coil, or cable, since the body of the medical device (e.g., lead) may serve this purpose. Similarly, those skilled in the art will recognize that the filars, wires, and cables described herein may be used to couple other types of elements besides connectors and electrodes, such as sensors, or any other type of component that is intended to transmit, receive, or conduct an electrical signal. Moreover, the disclosed embodiments need not be limited to use in medical electrical leads, but may be used in any other type of medical apparatus carrying such elements, such as catheters. Thus, the embodiments discussed above are merely exemplary, with the scope to be defined by the Claims that follow.

What is claimed is:

1. An implantable medical device (IMD), comprising:
   a coil comprising multiple filars, each being formed of a biocompatible beta titanium alloy having an elastic modulus ranging from 30 GigaPascals (GPa) to 90 GPa and comprising at least two elements from a group consisting of titanium, molybdenum, niobium, tantalum, zirconium, chromium, iron and tin, at least one of the multiple filars being electrically insulated from other ones of the filars; and
   a structural body carrying the coil.

2. The IMD of claim 1, wherein a ratio of pitch of the coil to outer diameter of the coil is greater than one.

3. The IMD of claim 2, wherein the coil comprises at least four filars.

4. The IMD of claim 3, wherein the coil has a pitch of greater than 0.03 inches.

5. The IMD of claim 3, wherein the coil has a pitch of greater than 0.06 inches.

6. The IMD of claim 4, wherein the coil comprises at least eight filars.

7. The IMD of claim 4, wherein the coil comprises twelve filars.

8. The IMD of claim 1, wherein a ratio of pitch of the coil to outer diameter of the coil is greater than two.

9. The IMD of claim 1, wherein the coil has an outer diameter of less than 0.03 inches.

10. The IMD of claim 1, wherein each of the filars carries a respective layer of insulating material to electrically insulate the filar from all others filars.

11. The IMD of claim 10, further comprising multiple elements carried by the structural body, each of the elements being electrically coupled to a different respective one of the filars.

12. The IMD of claim 10, further comprising at least eight electrodes, each of the at least eight electrodes being electrically coupled to a different respective one of the filars.

13. The IMD of claim 12, wherein the at least eight electrodes are segmented electrodes.

14. The IMD of claim 11, wherein at least one of the filars includes a low-resistance core, wherein a ratio of a cross-sectional area of the core to a cross-sectional area of the filar is selected to tune a resistance of the filar to a resistance of a respective one of the elements.

15. The IMD of claim 1, wherein each of the multiple filars includes a respective low-resistance core.

16. The IMD of claim 15, wherein each of the low-resistance cores is formed of a material having a resistivity of less than 25 micro-ohm-cm.

17. The IMD of claim 16, wherein the low-resistance core is formed of silver, tantalum, a tantalum alloy, niobium, a niobium alloy, platinum, a platinum alloy, palladium, or a palladium alloy.

18. The IMD of claim 1, wherein the coil defines an inner space, and further comprising a steering device positioned within the inner space.

19. A method, comprising:
   winding a coil of multiple filars, each being formed of a biocompatible beta titanium alloy having an elastic modulus ranging from 30 GigaPascals (GPa) to 90 GPa and comprising at least two elements from a group consisting of titanium, molybdenum, niobium, tantalum, zirconium, chromium, iron and tin; and
   providing at least one of the filars with an insulating layer to electrically insulate the filar from the other filars.

20. The method of claim 19, wherein a ratio of pitch of the coil to outer diameter of the coil is greater than one.

21. The method of claim 20, wherein the coil comprises at least four filars.

22. The method of claim 21, wherein the coil has a pitch of greater than 0.03 inches.

23. The method of claim 21, wherein the coil has a pitch of greater than 0.06 inches.

24. The method of claim 23, wherein the coil comprises at least eight filars.

25. The method of claim 23, wherein the coil comprises twelve filars.

26. The method of claim 19, wherein a ratio of pitch of the coil to outer diameter of the coil is greater than two.

27. The method of claim 19, wherein the coil has an outer diameter of less than 0.03 inches.

28. The method of claim 19, further comprising providing each of the filars with an insulating layer to electrically insulate each filar from all other filars.

29. The method of claim 28, further comprising:
providing at least eight electrodes; and
electrically coupling each of the filars to a different respective one of the electrodes.

30. The method of claim 28, further comprising:
incorporating the coil into a medical device adapted to perform at least one of delivering therapy to a patient or sensing a signal from the patient; and
electrically coupling one or more of the filars each to a different respective one of multiple elements carried by the medical device.

31. The method of claim 30, further comprising tuning a resistance of the one or more of the filars to each have substantially a same resistance as a resistance of the respective element to which the filar is electrically coupled.

32. The method of claim 31, wherein tuning a resistance comprises:
providing a low-resistance core;
providing a layer of the beta titanium alloy surrounding the low-resistance core to form a filar; and
wherein a ratio of an outer diameter of the core to an outer diameter of the filar is selected to obtain a selected resistance for the filar.

33. A medical electrical lead, comprising:
a lead body; and
a coil comprising multiple filars, each being formed of a biocompatible beta titanium alloy having an elastic modulus ranging from 30 GigaPascals (GPa) to 90 GPa and comprising at least two elements from a group consisting of titanium, molybdenum, niobium, tantalum, zirconium, chromium, iron and tin, at least one of the multiple filars being electrically insulated from other ones of the filars.

34. The medical electrical lead of claim 33, further comprising at least four electrodes, each being electrically coupled to a different respective one of the multiple filars.

35. The medical electrical lead of claim 33, further comprising at least eight electrodes, each being electrically coupled to a different respective one of the multiple filars.

36. The medical electrical lead of claim 35, wherein a ratio of pitch of the coil to outer diameter of the coil is greater than two.

37. The medical electrical lead of claim 35, wherein the outer diameter of the coil is less than 0.03 inches.

38. The medical electrical lead of claim 33, wherein the coil comprises twelve filars.

39. The medical electrical lead of claim 38, wherein the ratio of pitch of the coil to outer diameter of the coil is at least three.

40. The medical electrical lead of claim 33, wherein the coil has more than four filars and wherein the bend radius at yield for the coil is less than 0.15 inches.

* * * * *